(12) United States Patent
Boukhny et al.

(10) Patent No.: US 7,713,202 B2
(45) Date of Patent: May 11, 2010

(54) METHOD OF CONTROLLING A SURGICAL SYSTEM BASED ON A LOAD ON THE CUTTING TIP OF A HANDPIECE

(75) Inventors: Mikhail Boukhny, Laguna Niguel, CA (US); James Y. Chon, Irvine, CA (US); Ahmad Salehi, Irvine, CA (US); Ann Yadlowsky, Irvine, CA (US)

(73) Assignee: Alcon, Inc., Hunenberg (CH)

( * ) Notice: Subject to any disclaimer, the term of this patent is extended or adjusted under 35 U.S.C. 154(b) by 1323 days.

(21) Appl. No.: 11/189,492

(22) Filed: Jul. 26, 2005

(65) Prior Publication Data

US 2005/0261715 A1 Nov. 24, 2005

Related U.S. Application Data

(63) Continuation-in-part of application No. 11/068,301, filed on Feb. 28, 2005, now Pat. No. 7,625,388, which is a continuation-in-part of application No. 10/818,314, filed on Apr. 5, 2004, now Pat. No. 7,297,137.

(60) Provisional application No. 60/555,240, filed on Mar. 22, 2004, provisional application No. 60/587,693, filed on Jul. 14, 2004.

(51) Int. Cl.
*A61B 8/00* (2006.01)

(52) U.S. Cl. .................................................... 600/439

(58) Field of Classification Search ............. 604/19–22, 604/65–67; 128/DIG. 12, DIG. 13; 606/169, 606/170, 171; 600/437, 439, 471
See application file for complete search history.

(56) References Cited

U.S. PATENT DOCUMENTS

| 3,526,219 | A | 9/1970 | Balamuth |
| 3,589,363 | A | 6/1971 | Banko et al. |
| 3,601,126 | A | 8/1971 | Estes et al. |
| 3,693,613 | A | 9/1972 | Kelman |

(Continued)

FOREIGN PATENT DOCUMENTS

EP 359217 3/1990

(Continued)

OTHER PUBLICATIONS

Shuyu, Lin. "Sandwiched Piezoelectric Ultrasonic Transducers of Longitudinal—Torsional Compound Vibrational Modes." IEEE Transactions of Ultrasonics, Ferroelectrics and Frequency Control, Nov. 1997, pp. 1189-1197.

(Continued)

*Primary Examiner*—Manuel A Mendez
(74) *Attorney, Agent, or Firm*—Kenneth D. Bassinger

(57) ABSTRACT

A surgical system that is able to sense the onset of an occlusion or other surgical event as well as the instant an occlusion breaks. To help avoid overheating of the tip, the system determines an approximate temperature of the eye using an irrigation flow rate and reduces the power to the handpiece automatically if an overheating situation is predicted. Alternatively or in addition, the system monitors the power drawn by the handpiece, which is indicative of the cutting load on the tip, and automatically adjusts the power to the tip to compensate for increased loads on the tip.

17 Claims, 16 Drawing Sheets

U.S. PATENT DOCUMENTS

| | | |
|---|---|---|
| 3,812,855 A | 5/1974 | Banko |
| 3,812,858 A | 5/1974 | Oringer |
| 3,857,387 A | 12/1974 | Shock |
| 3,902,495 A | 9/1975 | Weiss et al. |
| 3,930,505 A | 1/1976 | Wallach |
| 3,942,519 A | 3/1976 | Shock |
| 3,952,732 A | 4/1976 | Shock |
| 3,956,826 A | 5/1976 | Perdreaux, Jr. |
| 3,964,487 A | 6/1976 | Judson |
| 3,990,452 A | 11/1976 | Murry et al. |
| 4,024,467 A | 5/1977 | Andrews et al. |
| 4,024,866 A | 5/1977 | Wallach |
| 4,114,623 A | 9/1978 | Meinke et al. |
| 4,126,137 A | 11/1978 | Archibald |
| 4,156,187 A | 5/1979 | Murry et al. |
| 4,168,707 A | 9/1979 | Douvas et al. |
| 4,184,510 A | 1/1980 | Murry et al. |
| 4,223,676 A | 9/1980 | Wuchinich |
| 4,246,902 A | 1/1981 | Martinez |
| 4,248,232 A | 2/1981 | Engelbrecht et al. |
| 4,406,284 A | 9/1983 | Banko |
| 4,417,578 A | 11/1983 | Banko |
| 4,493,694 A | 1/1985 | Wuchinich |
| 4,496,342 A | 1/1985 | Banko |
| 4,504,264 A | 3/1985 | Kelman |
| 4,508,532 A | 4/1985 | Drews et al. |
| 4,515,583 A | 5/1985 | Sorich |
| 4,589,415 A | 5/1986 | Haaga |
| 4,590,935 A | 5/1986 | Ranalli |
| 4,609,368 A | 9/1986 | Dotson, Jr. |
| 4,651,280 A | 3/1987 | Chang et al. |
| 4,658,819 A | 4/1987 | Harris et al. |
| 4,705,500 A | 11/1987 | Reimels et al. |
| 4,712,544 A | 12/1987 | Ensslin |
| 4,739,759 A | 4/1988 | Rexroth et al. |
| 4,750,488 A | 6/1988 | Wuchinich et al. |
| 4,770,654 A | 9/1988 | Rogers et al. |
| 4,793,346 A | 12/1988 | Mindich |
| 4,827,911 A | 5/1989 | Broadwin et al. |
| 4,869,715 A | 9/1989 | Sherburne |
| 4,922,902 A | 5/1990 | Wuchinich et al. |
| 4,961,424 A | 10/1990 | Kubota et al. |
| 4,969,885 A | 11/1990 | Farin |
| 4,989,583 A | 2/1991 | Hood |
| 4,989,588 A | 2/1991 | Kubota et al. |
| 5,026,387 A | 6/1991 | Thomas |
| 5,116,343 A | 5/1992 | Ames et al. |
| 5,139,509 A | 8/1992 | Fischer et al. |
| 5,151,085 A | 9/1992 | Sakurai et al. |
| 5,154,694 A | 10/1992 | Kelman |
| 5,154,696 A | 10/1992 | Shearing |
| 5,160,317 A | 11/1992 | Costin |
| 5,180,363 A | 1/1993 | Idemoto et al. |
| 5,188,102 A | 2/1993 | Idemoto et al. |
| 5,188,589 A | 2/1993 | Wypych et al. |
| 5,205,817 A | 4/1993 | Idemoto et al. |
| 5,222,959 A | 6/1993 | Anis |
| 5,242,385 A | 9/1993 | Strukel |
| 5,279,547 A | 1/1994 | Costin |
| 5,304,115 A | 4/1994 | Pflueger et al. |
| 5,342,293 A | 8/1994 | Zanger |
| 5,359,996 A | 11/1994 | Hood |
| 5,431,664 A | 7/1995 | Ureche et al. |
| 5,520,633 A | 5/1996 | Costin |
| 5,569,188 A | 10/1996 | Mackool |
| 5,591,127 A | 1/1997 | Barwick, Jr. et al. |
| 5,676,649 A | 10/1997 | Boukhny et al. |
| 5,700,240 A | 12/1997 | Barwick, Jr. et al. |
| 5,722,945 A | 3/1998 | Anis et al. |
| 5,733,256 A | 3/1998 | Costin |
| 5,766,146 A | 6/1998 | Barwick, Jr. |
| 5,808,396 A | 9/1998 | Boukhny |
| 5,865,790 A | 2/1999 | Bair |
| 6,027,515 A | 2/2000 | Cimino |
| 6,028,387 A | 2/2000 | Boukhny |
| 6,077,285 A | 6/2000 | Boukhny |
| 6,083,193 A | 7/2000 | Kadziauskas et al. |
| 6,175,180 B1 | 1/2001 | Angelini et al. |
| 6,179,805 B1 | 1/2001 | Sussman et al. |
| 6,179,808 B1 | 1/2001 | Boukhny et al. |
| 6,193,683 B1 | 2/2001 | Ludin et al. |
| 6,261,283 B1 | 7/2001 | Morgan et al. |
| 6,261,297 B1 | 7/2001 | Kadziauskas et al. |
| 6,283,974 B1 | 9/2001 | Alexander |
| 6,315,755 B1 | 11/2001 | Sussman |
| 6,394,974 B1 | 5/2002 | Kadziauskas et al. |
| 6,402,769 B1 | 6/2002 | Boukhny |
| 6,629,948 B2 | 10/2003 | Rockley |
| 6,699,212 B1 | 3/2004 | Kadziauskas |
| 6,780,165 B2 | 8/2004 | Kadziauskas |
| 7,374,552 B2 | 5/2008 | Wuchinich |
| 2001/0001123 A1 | 5/2001 | Madan et al. |
| 2001/0011176 A1 | 8/2001 | Boukhny |
| 2003/0045887 A1 | 3/2003 | Sakurai et al. |
| 2004/0092800 A1 | 5/2004 | Mackool |
| 2004/0092922 A1 | 5/2004 | Kadziauskas et al. |
| 2006/0041200 A1 | 2/2006 | Dotter et al. |

FOREIGN PATENT DOCUMENTS

| | | |
|---|---|---|
| WO | 8705793 | 10/1987 |
| WO | WO 92/07622 | 5/1992 |
| WO | WO 99/18901 | 4/1999 |
| WO | WO 99/45868 | 9/1999 |
| WO | WO 01/41672 | 6/2001 |
| WO | WO 01/97728 A1 | 12/2001 |
| WO | WO 2004/080505 | 9/2004 |

OTHER PUBLICATIONS

Jiromaru Tsujino, "Ultrasonic Motor Using A One-Dimensional Longitudinal—Torsional Vibration Converter With Diagonal Slits", Smart Mater. Struct. 7 (1998) 345-351.

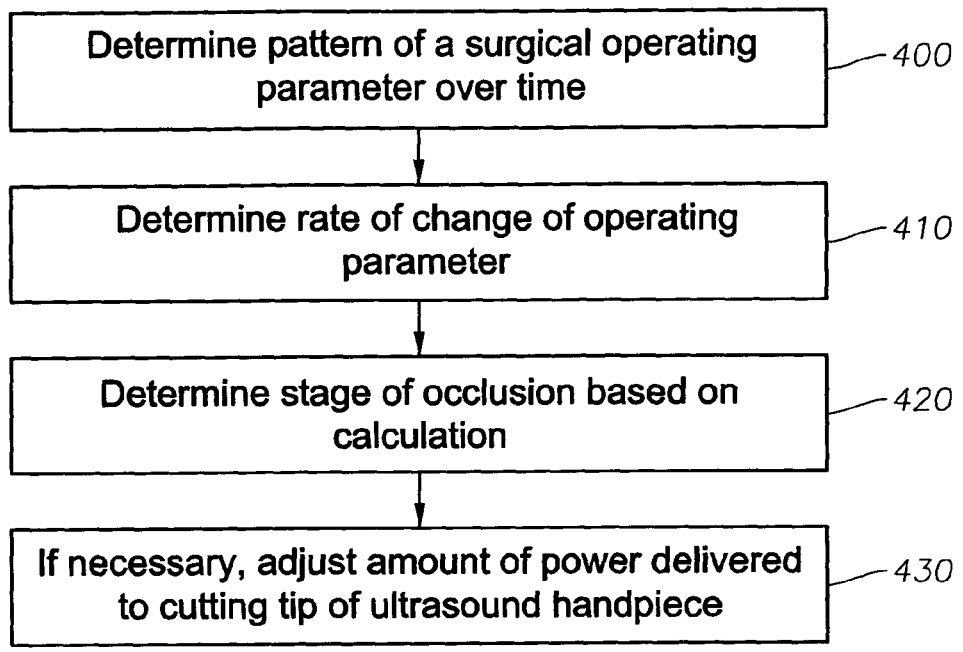
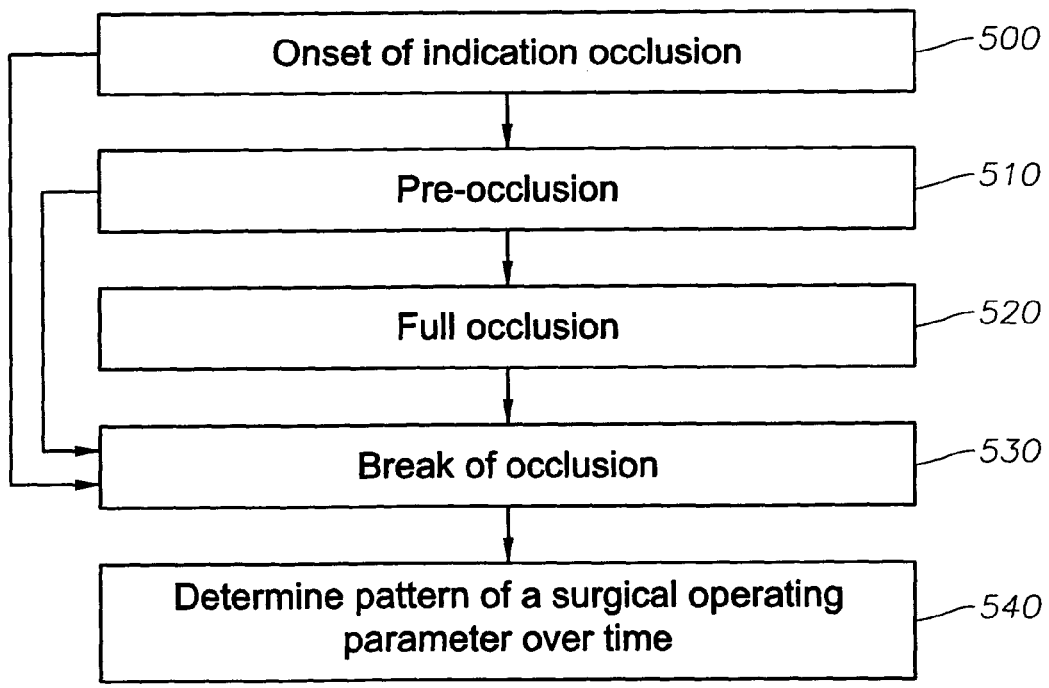

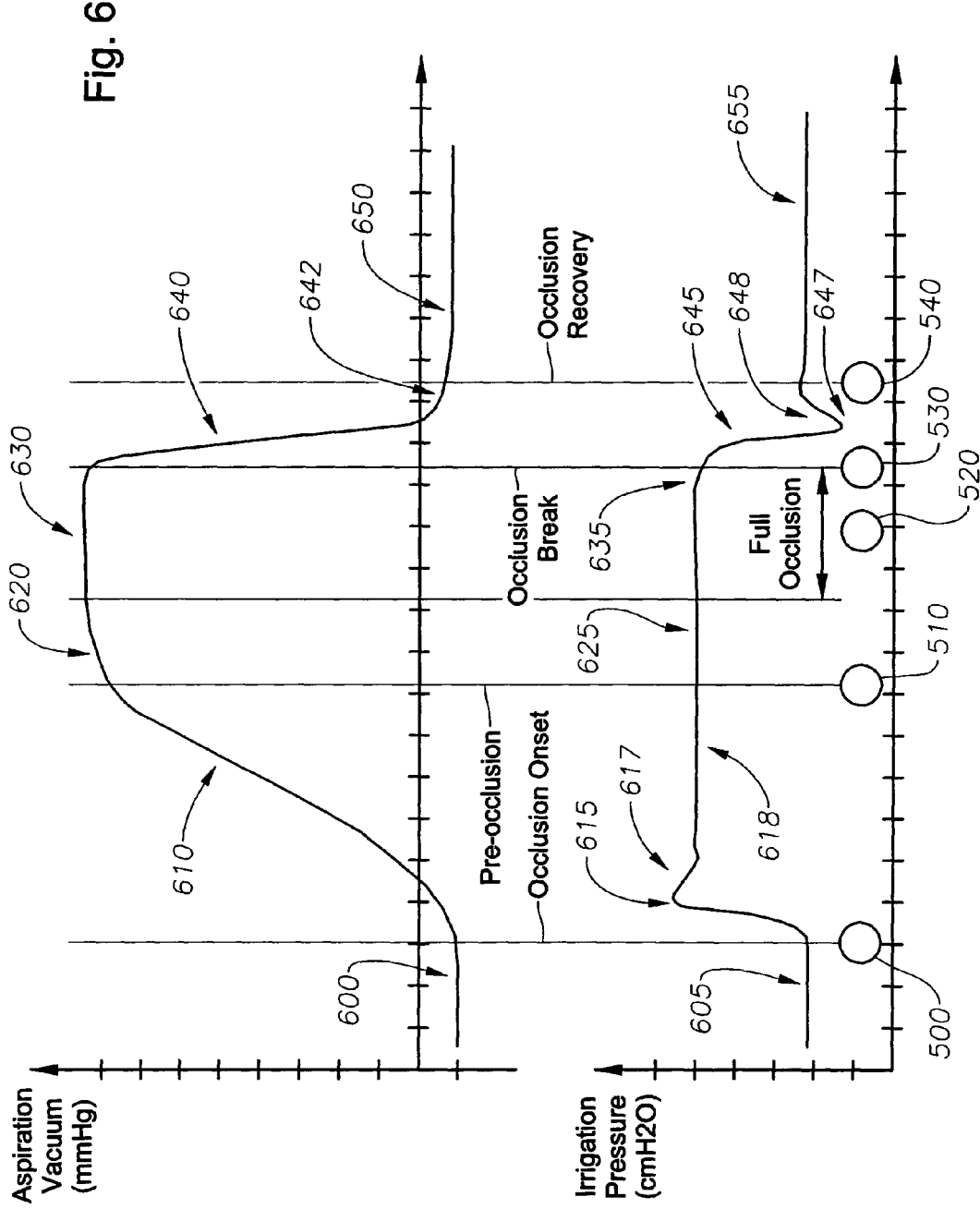

(Smaller Load/Smaller Decay)

(Larger Load/Faster Decay)

METHOD OF CONTROLLING A SURGICAL SYSTEM BASED ON A LOAD ON THE CUTTING TIP OF A HANDPIECE

CROSS REFERENCE TO RELATED APPLICATIONS

This application is a continuation-in-part of U.S. patent application Ser. No. 11/068,301, filed Feb. 28, 2005, now U.S. Pat. No. 7,625,388, which is a continuation-in-part of U.S. patent application Ser. No. 10/818,314, filed Apr. 5, 2004, now U.S. Pat. No. 7,297,137, priority to which is claimed under 35 U.S.C. §120, which claims priority to U.S. Provisional Application Ser. No. 60/555,240, filed Mar. 22, 2004, under 35 U.S.C. §119. This application also claims priority under 35 U.S.C. §119 to U.S. Provisional Application Ser. No. 60/587,693, filed Jul. 14, 2004.

FIELD OF THE INVENTION

The present invention relates generally to the field of ophthalmic surgery and, more particularly, to a method of controlling surgical parameters of a pharcoemulsification system.

BACKGROUND

The human eye functions to provide vision by transmitting light through a clear outer portion called the cornea, and focusing the image by way of the lens onto the retina. The quality of the focused image depends on many factors including the size and shape of the eye, and the transparency of the cornea and lens. When age or disease causes the lens to become less transparent, vision deteriorates because of the diminished light which can be transmitted to the retina. This deficiency is medically known as a cataract. An accepted treatment for cataracts is to surgically remove the cataract and replace the lens with an artificial intraocular lens (IOL). In the United States, the majority of cataractous lenses are removed using a surgical technique called phacoemulsification. During this procedure, a thin cutting tip is inserted into the diseased lens and vibrated ultrasonically. The vibrating cutting tip liquefies or emulsifies the lens so that the lens may be aspirated out of the eye. The diseased lens, once removed, is replaced by an IOL.

A typical ultrasonic surgical device suitable for an ophthalmic procedure includes an ultrasonically driven handpiece, an attached cutting tip, an irrigating sleeve and an electronic control console. The handpiece assembly is attached to the control console by an electric cable or connector and flexible tubings. A surgeon controls the amount of ultrasound power that is delivered to the cutting tip of the handpiece and applied to tissue at any given time by pressing a foot pedal to request power up to the maximum amount of power set on the console. Flexible tubings supply irrigation fluid to and draw aspiration fluid from the eye through the handpiece assembly.

The operative part of the handpiece is a centrally located, hollow resonating bar or horn that is attached to a set of piezoelectric crystals. The crystals are controlled by the console and supply ultrasonic vibrations that drive both the horn and the attached cutting tip during phacoemulsification. The crystal/horn assembly is suspended within the hollow body or shell of the handpiece by flexible mountings. The handpiece body terminates in a reduced diameter portion or nosecone at the body's distal end. The nosecone is externally threaded to accept the irrigation sleeve. Likewise, the horn bore is internally threaded at its distal end to receive the external threads of the cutting tip. The irrigation sleeve also has an internally threaded bore that is screwed onto the external threads of the nosecone. The cutting tip is adjusted so that the tip projects only a predetermined amount past the open end of the irrigating sleeve.

In use, the ends of the cutting tip and the irrigating sleeve are inserted into a small incision of predetermined width in the cornea, sclera, or other location. One known cutting tip is ultrasonically vibrated along its longitudinal axis within the irrigating sleeve by the crystal-driven ultrasonic horn, thereby emulsifying the selected tissue in situ. The hollow bore of the cutting tip communicates with the bore in the horn that in turn communicates with the aspiration line from the handpiece to the console. Other suitable cutting tips include piezoelectric elements that produce both longitudinal and torsional oscillations. One example of such a cutting tip is described in U.S. Pat. No. 6,402,769 (Boukhny), the contents of which are incorporated herein by reference.

A reduced pressure or vacuum source in the console draws or aspirates the emulsified tissue from the eye through the open end of the cutting tip, the cutting tip and horn bores and the aspiration line, and into a collection device. The aspiration of emulsified tissue is aided by a saline solution or other irrigant that is injected into the surgical site through the small annular gap between the inside surface of the irrigating sleeve and the cutting tip.

One known surgical technique is to make the incision into the anterior chamber of the eye as small as possible in order to reduce the risk of induced astigmatism. These small incisions result in very tight wounds that squeeze the irrigating sleeve tightly against the vibrating tip. Friction between the irrigating sleeve and the vibrating tip generates heat. The risk of the tip overheating and burning tissue is reduced by the cooling effect of the aspirated fluid flowing inside the tip.

When the tip becomes occluded or clogged with emulsified tissue, the aspiration flow can be reduced or eliminated, allowing the tip to heat up, thereby reducing cooling and resulting in temperature increase, which may burn the tissue at the incision. In addition, during occlusion, a larger vacuum can build up in the aspiration tubing so that when the occlusion eventually breaks, a larger amount of fluid can be quickly suctioned from the eye, possibly resulting in the globe collapsing or other damage to the eye.

Known devices have used sensors that detect large rises in aspiration vacuum, and detect occlusions based a particular pre-determined aspiration vacuum level. Based on this sensed occlusion, power to the handpiece may be reduced and/or irrigation and aspiration flows can be increased. See U.S. Pat. Nos. 5,591,127, 5,700,240 and 5,766,146 (Barwick, Jr., et al.), the entire contents of which are incorporated herein by reference. These devices, however, use a fixed aspiration vacuum level to trigger a response from the system. This fixed level is a threshold value based upon a fixed percentage of the selected upper vacuum limit. The use and effectiveness of such systems, however, are limited since they do not respond until that preset aspiration vacuum level is reached. U.S. Pat. No. 6,179,808 to Boukhny, et. al., the entire contents of which are incorporated herein by reference, describes a system that reduces signal amplitude and/or duty cycle when the temperature exceeds a predetermined limit, as calculated based on the measured or estimated irrigation flow.

Known occlusion sensing systems can thus be improved since, in reality, aspiration vacuum levels can vary over a short period of time during different stages of occlusion. Setting this preset vacuum limit too low results in the system changing its operating parameters prematurely, and holding on to those parameters after the occlusion has cleared. Setting the limit too high can result in the system changing its setting too close to the actual occurrence of the occlusion, and changing its setting back to normal prior to the clearance of the occlusion. In addition, cutting efficiency is maximized when the cutting tip is occluded, so increasing power when an occluded condition is detected maximizes cutting efficiency, but increases the risk of overheating the tissue surrounding the tip.

Further, throughout the surgery, there are times when the tip is pressing against the lens in order to emulsify lens tissue, and there are times when the tip is not in contact with the lens. Ultrasound energy, however, remains on until the surgeon releases the foot pedal, even during times when the lens material is aspirated, the surgeon pulls the tip away from the lens, or the lens moves away from the tip. The efficiency of the surgery decreases, and the wasted energy can cause unnecessary heating of the tip, which may increase the likelihood of an undesirable burn to the tissue at the incision.

Therefore, a need continues to exist for an occlusion detection system that more accurately detects the occurrence and clearance of an occlusion in a surgical aspiration system. This information can be used by the control system to adjust power accordingly, e.g., increasing power during an occlusion in order to improve the cutting efficiency of the ultrasound tip and/or reducing power when the relative temperature reaches a predetermined threshold in order to prevent excessive heating. Cutting efficiency may be further increased by adding a load detection system that detects when the tip is no longer in contact with lens material and adjusts power automatically.

SUMMARY

According to one embodiment, a method of controlling a surgical system includes establishing a threshold power level, monitoring a load on the cutting tip of an ultrasound handpiece based on the voltage and current drawn by the handpiece during a non-zero sense power interval that is between cutting power intervals. The power drawn by the handpiece is compared to the threshold power level and is adjusted as necessary, for example, if the power drawn by the handpiece exceeds the threshold power level by adjusting an amplitude or stroke of the output of the ultrasound handpiece or by enabling torsional vibration of the tip.

In an alternative embodiment, a method of controlling a surgical system includes establishing a threshold power level and monitoring a load on the cutting tip of an ultrasound handpiece based on the voltage and current drawn by the handpiece during a non-zero sense power interval that is between cutting power intervals. The power drawn by the handpiece is compared to the threshold power level, and adjusted as necessary. Further, a threshold temperature is established, and the irrigation pressure in the line running to the handpiece is monitored. A rate of flow of irrigation fluid is calculated and the heat absorption capacity of the irrigation fluid flow is determined. The heat absorption capacity and power supplied to the handpiece are compared or analyzed to determine a temperature of an eye, which is compared to the threshold temperature. The power delivered to the cutting tip of the handpiece is adjusted as necessary.

According to another embodiment, a method of controlling a surgical system includes establishing a threshold power level and monitoring a load on the cutting tip of the ultrasound handpiece based on the voltage and current drawn by the handpiece during a non-zero sense power interval that is between cutting power intervals. The power drawn by the handpiece is compared to the threshold power level and adjusted if the power drawn by the handpiece exceeds the threshold power level. Power can be adjusted by changing the amplitude or stroke or by enabling torsional vibration of the ultrasound handpiece. In addition, a rate of change of an operating parameter of the surgical system is determined, and a stage of occlusion is determined based on the rate of change. The power delivered to the cutting tip of the handpiece is adjusted as necessary based on the determined stage of occlusion.

In various embodiments, the load monitoring is performed during a sense interval or pulse at a power level that is less than the power level of cutting pulses and by monitoring voltage and current. Voltage and current can be monitored during a substantially constant portion of a pulse or interval or during a decay of a sense interval or pulse. The sense pulse or interval can have a fixed or variable duration. Sense pulses or intervals can immediately precede or follow cutting pulses, or can be pulses or intervals that are separate from cutting pulses. Load monitoring can also be performed by during a decay of a non-zero sense power interval. Some degree of cutting may occur, since a sense interval is at a relatively low power level.

Power can be adjusted by adjusting a stroke of the cutting pulse or interval following a non-zero sense interval. In various embodiments, power adjustments may be made by adjusting a duty cycle of the output of the ultrasound handpiece. A sensitivity adjustment can be used to adjust the amount of power that is delivered to the cutting tip.

Power adjustments can also be related to comparisons of calculating flow rates of irrigation fluid and determining a heat absorption capacity to determine a temperature of an eye, which is compared to a threshold temperature to determine whether power should be adjusted.

BRIEF DESCRIPTION OF THE DRAWINGS

Referring now to the drawings, in which like reference numbers represent corresponding parts throughout and in which:

FIG. 4 is a flow diagram illustrating one embodiment of a method of adjusting power delivered to a handpiece power based on a pattern and a rate of change of one or more operating parameters;

FIG. 5 illustrates the stages of occlusion that can be used with the embodiments of the present invention;

FIG. 6 illustrates patterns of aspiration vacuum and irrigation pressure at different stages of an occlusion shown in FIG. 5;

DETAILED DESCRIPTION OF ILLUSTRATED EMBODIMENTS

This specification describes embodiments of a method for controlling a surgical system for use in, for example, phacoemulsification surgery. Embodiments provide a surgical system that is able to detect stages of a surgical event, such as an occlusion, e.g., the onset of an occlusion, a pre-occlusion condition, a full occlusion, and when an occlusion breaks, by detecting changes in the pressure levels of an aspiration system, an irrigation system, or a combination thereof. By monitoring how the aspiration vacuum or irrigation pressure levels vary, the onset and break up of an occlusion can be accurately detected. Once an occlusion is detected, the surgical system can be programmed to vary the power available to the handpiece, either by changing the stroke of the tip or by changing the duty cycle of the pulsed ultrasound power or by enabling torsional vibration of the tip.

To help avoid overheating of the tip, the surgical system monitors the irrigation flow rate and reduces the power to the handpiece automatically if an overheating situation is predicted. Alternatively, or in addition, the amount of power drawn by the handpiece can be monitored, which indicates the cutting load on the tip. This information can be used to automatically adjust the power or stroke (displacement) of the tip or to enable torsional vibration of the tip to compensate for load variations on the tip. In the following description, reference is made to the accompanying drawings, which show by way of illustration, but not limitation, specific embodiments that can be utilized.

Figure 1:
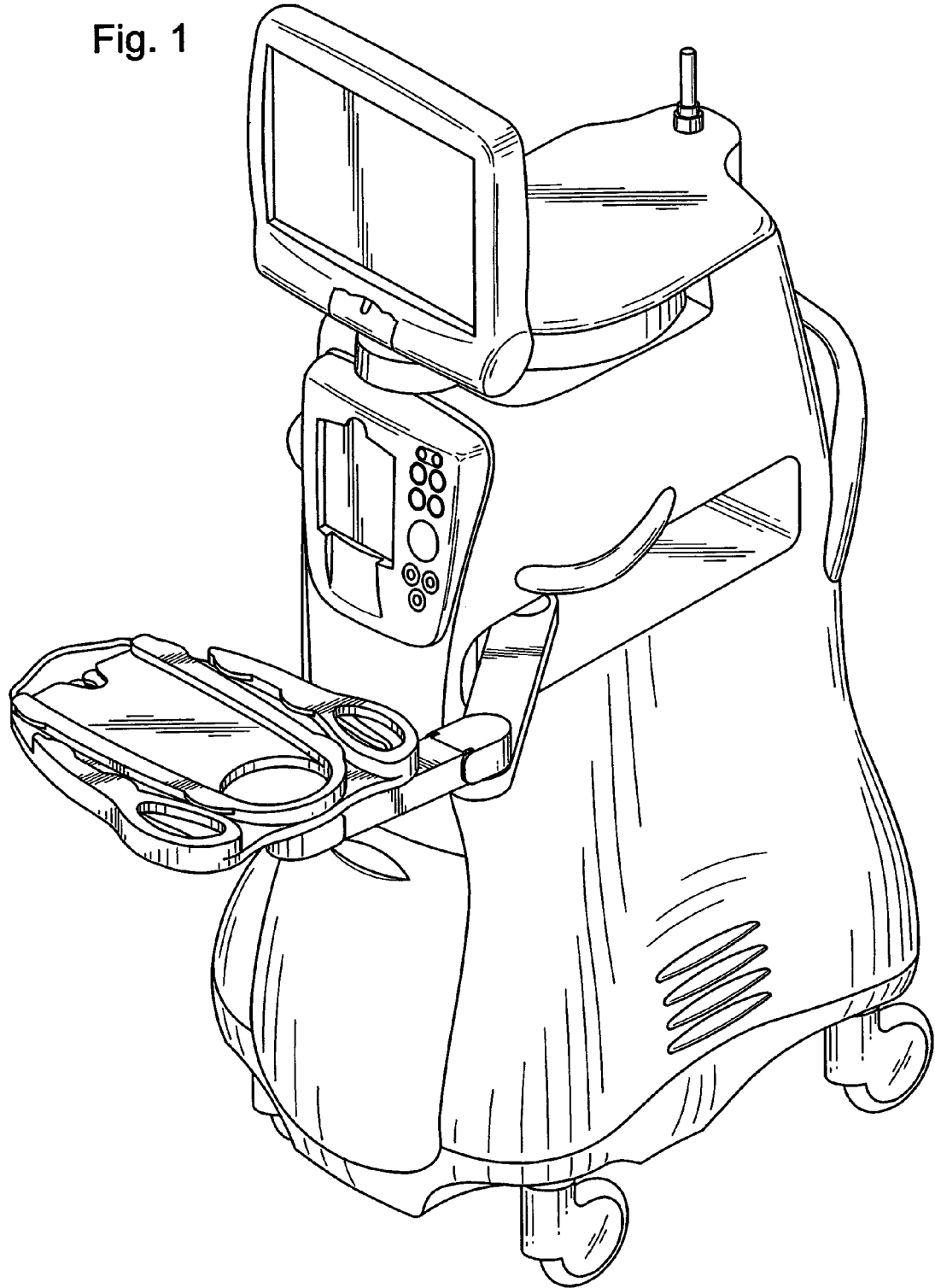
FIG. 1 is a perspective view of an exemplary surgical system that may be used with various embodiments.

Embodiments can be implemented on commercially available surgical systems or consoles through appropriate hardware and software controls. One suitable system 100 is generally illustrated in FIG. 1 and represents the INFINITI® Vision System available from Alcon Laboratories, Inc., 6201 South Freeway, Q-148, Fort Worth, Tex. 76134.

Figure 2:
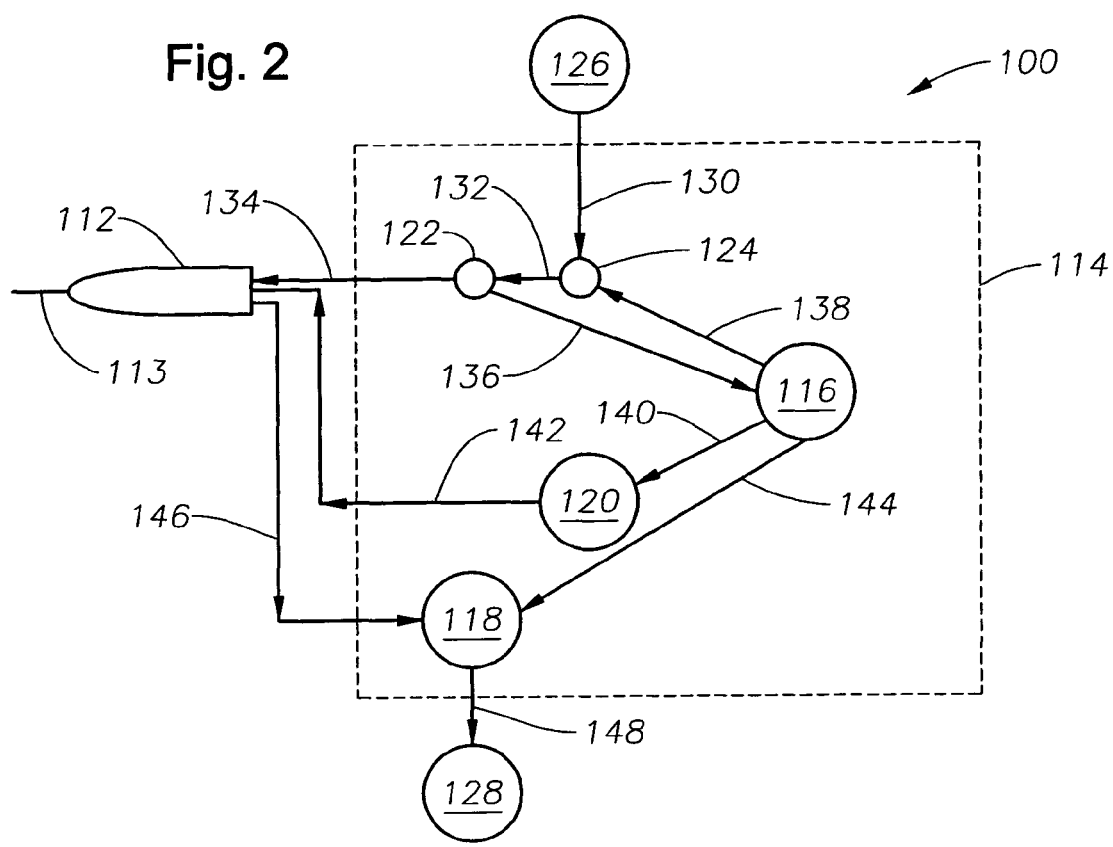
FIG. 2 is block diagram showing components of a surgical system.

FIG. 2 illustrates one exemplary control system 100 in further detail. The control system 100 is used to operate an ultrasound handpiece 112 and includes a control console 114, which has a control module or CPU 116, an aspiration, vacuum or peristaltic pump 118, a handpiece power supply 120, an irrigation pressure sensor ("IPS") 122 and a valve 124. The console 114 may be any commercially available surgical control console such as the ACCURUS® surgical system, also available from Alcon Laboratories, Inc. Although an irrigation pressure sensor is shown, one skilled in the art will recognize that instead of a pressure sensor, a flow sensor may also be used.

Figure 3A:
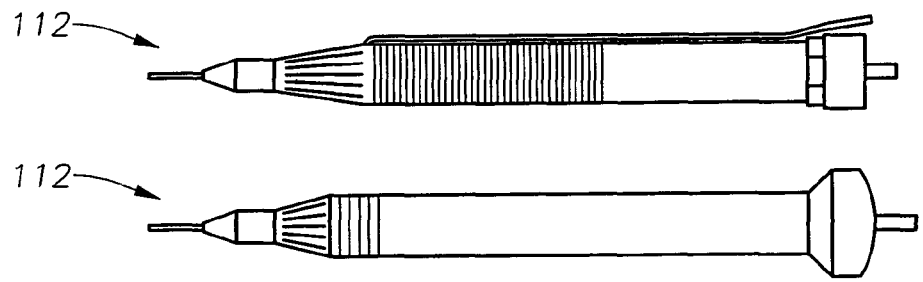
FIGS. 3A-B illustrate exemplary ultrasonic handpieces that can be used with various embodiments.
Figure 3B:
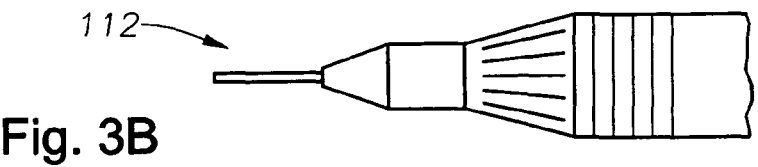

Various ultrasonic handpieces 112 and cutting tips can be utilized including, but not limited to, handpieces and tips described in U.S. Pat. Nos. 3,589,363; 4,223,676; 4,246,902; 4,493,694; 4,515,583; 4,589,415; 4,609,368; 4,869,715; 4,922,902; 4,989,583; 5,154,694 and 5,359,996, the entire contents of which are incorporated herein by reference. Exemplary handpieces are shown in FIGS. 3A-B for purposes of explanation, but not limitation.

Referring again to FIG. 2, the CPU 116 may be any suitable microprocessor, micro-controller, computer or digital logic controller. The pump 118 may be a peristaltic, a diaphragm, a Venturi or other suitable pump. The power supply 120 may be any suitable ultrasound driver, such as incorporated in the ACCURUS® surgical system, also available from Alcon Laboratories, Inc. The valve 124 may be any suitable valve such as a solenoid-activated pinch valve. An infusion of an irrigation fluid, such as saline, may be provided by a saline source 126, which may be any commercially available irrigation solution provided in bottles or bags.

In use, irrigation pressure sensor 122 is connected to the handpiece 112 and the infusion fluid source 126 through irrigation lines 130, 132 and 134. The irrigation pressure sensor 122 measures the pressure of irrigation fluid from the source 126 to the handpiece 112 and supplies this information to the CPU 116 through the cable 136. The irrigation fluid pressure data may be used by the CPU 116 to control the operating parameters of the console 114 using software commands. For example, the CPU 116 may, through a cable 140, vary the output of the power supply 120 being sent to the handpiece 112 and the tip 113 though a power cable 142. The CPU 116 may also use data supplied by the irrigation pressure sensor 122 to vary the operation of the pump 118 through a cable 144. The pump 118 aspirates fluid from the handpiece 112 through a line 146 and into a collection container 128 through line 148. The CPU 116 may also use data supplied by the irrigation pressure sensor 122 and the applied output of power supply 120 to provide audible tones to the user. Additional details concerning such surgical systems can be found in U.S. Pat. No. 6,179,808 (Boukhny, et al.) and U.S. Pat. No. 6,261,283 (Morgan, et al.), the entire contents of which are incorporated herein by reference.

In one embodiment, the control console 114 can control the amount of power that is delivered to the handpiece 112 based on the stage of an occlusion event. More particularly, power adjustments are made based on changes of an aspiration vacuum level, an irrigation pressure level, or both aspiration vacuum and irrigation pressure levels. The change can be, for example, a rate of change of the increase or decrease of aspiration vacuum and/or irrigation pressure.

Adjustments to the amount of power delivered to a handpiece can be made as shown in FIG. 4. Initially, in step 400, a pattern of a surgical operating parameter during an occlusion or other surgical event is detected over a period of time. The operating parameter can be aspiration vacuum and/or an irrigation pressure. Both pressures can also be detected, however, reference is primarily made to a single operating parameter for purposes of explanation, not limitation. In step 410, the values and/or the rate of change of the operating parameter can be determined or calculated. Based on this calculation, a stage of an occlusion is determined. In step 430, the amount of power that is delivered to a cutting tip of the handpiece 112 can be adjusted, as necessary, based on the stage of occlusion.

More specifically, it has been determined that aspiration vacuum and irrigation pressure levels follow a detectable pattern before, during and after an occlusion. This pattern can be used to identify a stage of an occlusion and adjust the power delivered to the handpiece 112 accordingly.

As shown in FIG. 5, a typical occlusion event has the following stages: occlusion onset 500; pre-occlusion 510; full occlusion 520; occlusion break 530; and recovery 540. The term "onset" is generally used to refer to the very beginning or preliminary stages of an occlusion, and "pre-occlusion" is generally used to refer to a time following an occlusion onset, and preceding full occlusion. In other words, "onset" is generally used to refer to the beginning of the development of an occlusion, and "pre-occlusion" is generally used to refer the stage where an occlusion is maturing to a full occlusion.

FIG. 6 illustrates in further detail patterns of aspiration vacuum and irrigation pressure that were detected. For each stage, the aspiration vacuum is shown as (mmHg) over time (t) and the pressure of an irrigation fluid or saline is shown as (cm $H_2O$) over the same time (t). These stages are discussed in further detail below.

As shown in FIG. 6, an occlusion onset event or condition 500 is characterized by a rapid increase 610 in the aspiration vacuum and a rapid increase 615 in the irrigation pressure from a state of non-occlusion during which the vacuum and irrigation pressures are relatively steady or constant (600 and 605). In other words, the rates at which the vacuum and irrigation pressures are increasing are >0. As shown, the onset 500 is identified by increasing aspiration vacuum and irrigation pressure. The irrigation pressure then may decrease slightly (617) and level off (618). The level of the aspiration vacuum, however, increases initially, and continues to increase while the irrigation pressure remains stable.

Following the occlusion onset event 500, the occlusion develops or matures into a pre-occlusion event or condition 510. As shown in FIG. 6, a pre-occlusion event 510 is characterized by a slowing 620 of the rate of increase in aspiration vacuum, and a relatively stabilized irrigation pressure 625. Thus, the rate of increase of the aspiration vacuum and the irrigation pressure both gradually decrease to a rate of zero. In other words, both the vacuum and irrigation pressures become relatively stable.

The pre-occlusion condition 510 matures into a full occlusion 520. A full occlusion is characterized by the maximum limit 630. Further, the irrigation pressure is steady 635.

Following the full occlusion 520, the occlusion breaks 530. An occlusion break event 530 is characterized by a rapid decrease of both the aspiration vacuum 640 and the irrigation pressure 645. As shown in FIG. 6, both the aspiration vacuum and irrigation pressure levels rapidly decrease (respective rates are <0) following a break of the occlusion. Following the rapid decrease, the rate of the decline of the aspiration vacuum and irrigation pressure level decrease 642, whereas the irrigation level pressure may reverse upward briefly 647 and then stabilize 648.

Following the occlusion break 520 is an occlusion recovery stage 530. A recovery stage 530 is characterized by a continued slowing of the rate of decrease of the aspiration vacuum 650 and irrigation pressure 655, eventually reaching a substantially constant level. In other words, the rates of decline of the vacuum and irrigation pressures gradually increase from a negative value to approximately 0.

Based on the surgical systems tested, the patterns of vacuum and irrigation pressures shown in FIG. 6 are consistent from surgical system to surgical system and can be detected using a variety of known digital signal processing methods. In one embodiment, the vacuum and irrigation pressures are detected using correlation methods. For example, phases of an occlusion can be detected by calculating a linear correlation between a pre-defined pattern and the actual aspiration vacuum or irrigation pressure sensor readings from the surgical system. The pre-defined pattern of aspiration vacuum defining occlusion onset can be, for example, four points of the same vacuum reading followed by 12 points of linearly increasing vacuum reading.

For example, the linear correlation between two sequences $x_i$ and $y_i$ is a measurement of how close one sequence can be transformed into the other via a linear transformation:

$$y_i a x_i + b$$

Where: a=linear correlation coefficient, b=offset.

Given two sequences, the linear correlation R is calculated as follows:

$$R = \frac{\sum_{i=0}^{N} x_i y_i - \frac{\sum_{i=0}^{N} x_i \sum_{i=0}^{N} y_i}{N}}{\sqrt{\sum_{i=0}^{N} x_i^2 - \frac{\left(\sum_{i=0}^{N} x_i\right)^2}{N}} \sqrt{\sum_{i=0}^{N} y_i^2 - \frac{\left(\sum_{i=0}^{N} y_i\right)^2}{N}}}$$

Where: N–correlation length (i.e. number of points in the sequences)

The linear correlation coefficient is calculated as follows:

$$a = \frac{\sum_{i=0}^{N} x_i y_i - \frac{\sum_{i=0}^{N} x_i \sum_{i=0}^{N} y_i}{N}}{\sum_{i=0}^{N} x_i^2 - \frac{\left(\sum_{i=0}^{N} x_i\right)^2}{N}}$$

A method according to one embodiment involves calculating the linear correlation between a sample sequence of aspiration vacuum and/or irrigation pressure sensor readings collected during use of the surgical system and the predefined pattern representing the occlusion events in question. The calculated correlation value reflects the similarity between the sample sequence and the predefined pattern, with the highest possible value of 1.0 representing an absolute match. The range of values indicating a sufficient correlation is preferably between 0.80 and 0.99.

Once a match or acceptable correlation is established, the certainty of the some surgical events, such as pre-occlusion and occlusion recovery is high, and the surgical parameters of the system can be adjusted as necessary.

For events such as occlusion onset and occlusion break, the pattern match should be qualified based on the rate of the change of the test values. The rate of change of vacuum and irrigation pressures can be evaluated using linear correlation coefficient, which reflects the slope ratio of the test sequence and the predefined pattern, and can thus be used to evaluate whether the sample sequence has a sufficient rate of change for a particular event.

In one embodiment, the rate of change is a direct calculation of the derivative (ΔValue/ΔTime), or the change in a value over a certain time. The criteria for a sufficient rate can be established empirically for a given system at different settings (e.g. different aspiration pump rates).

For cases that require qualification on both pattern match and the rate of change, the occlusion event is considered to be detected when both conditions are satisfied. Once the occlusion event is detected the surgical parameters of the system can be adjusted. The described method can be applied to detecting all events in an occlusion sequence (occlusion onset, pre-occlusion, occlusion, occlusion break, and recovery). By detecting patterns of aspiration vacuum and/or irrigation pressure levels, the timing of when power should be adjusted can be accurately determined. Thus, embodiments are more accurate than known systems that rely on a threshold or pre-determined aspiration vacuum levels to identify a full occlusion.

In a further embodiment, the matching of patterns can be accomplished using convolution rather than correlation. Accordingly, persons of ordinary skill in the art will appreciate that the correlation, derivative, and convolution techniques discussed herein are merely illustrative examples, and are not intended to be limiting.

Figure 7:
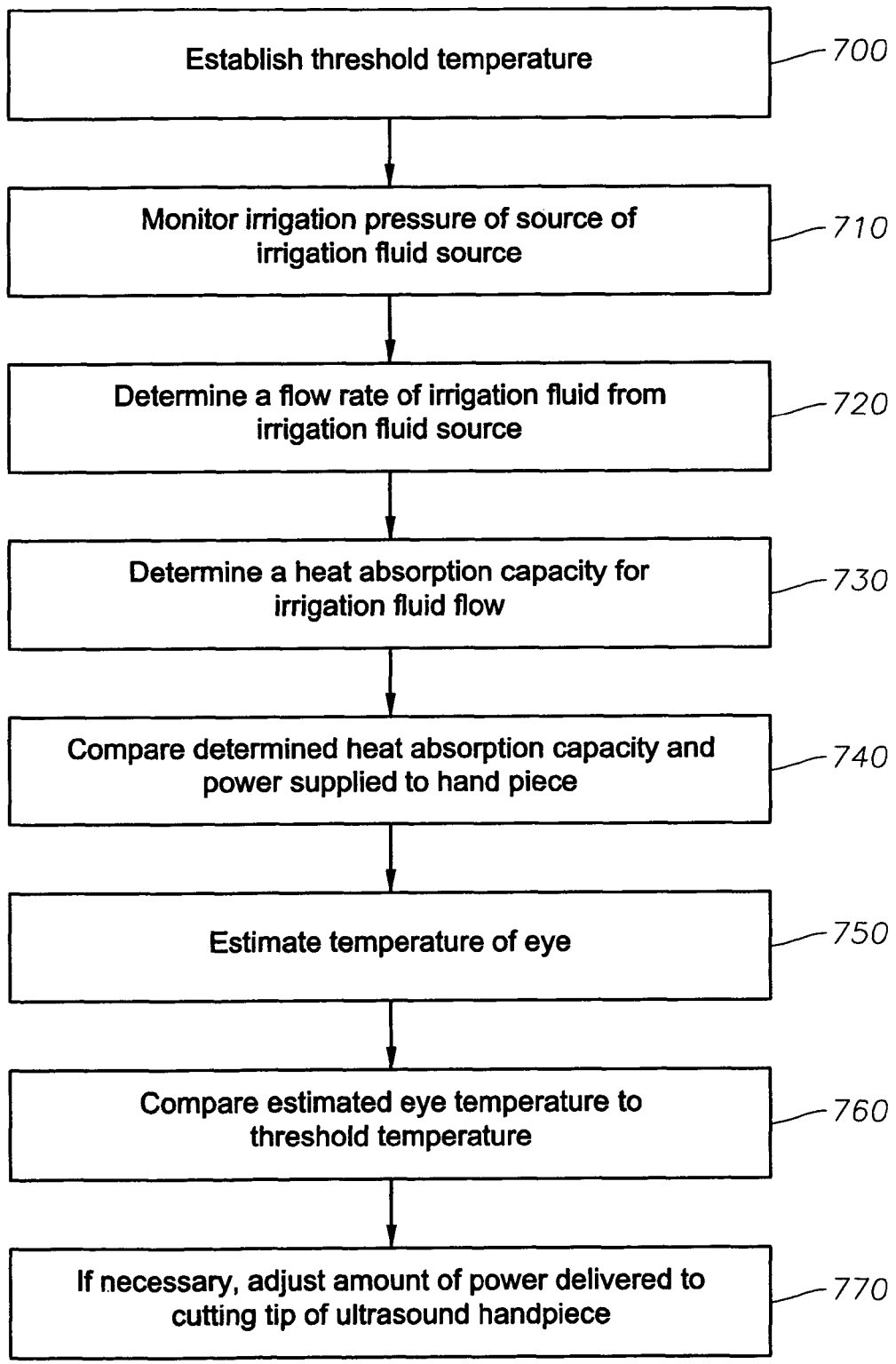
FIG. 7 is a flow diagram illustrating one embodiment of a method for adjusting power to prevent overheating of a transducer tip.

In a further embodiment, the amount of power delivered to the handpiece can be regulated to prevent overheating of the tip 113, which can lead to damage to the eye tissue. This embodiment is referred to as Thermal Watch™ and is generally illustrated in FIG. 7.

In step 700, a threshold temperature is established. In step 710, a pressure of a source of an irrigation fluid 126, such as saline, is monitored. In step 720, a calculation or determination is made of the flow rate of irrigation fluid from the irrigation fluid source 126 being monitored. A capacity of the flow of irrigation fluid to absorb heat, or the heat absorption capacity of the irrigation fluid, is determined in step 730. In step 740, the determined heat absorption capacity and the power supplied to the handpiece 112 are compared or analyzed. Based on this comparison or analysis, a temperature of the eye or other tissue is determined in step 750.

For example, an approximate temperature of the eye can be determined by performing a temperature calculation at discrete time steps where the estimated temperature at the current time is found by multiplying the previous temperature estimation by a cooling coefficient (which is <1) then adding the power delivered during the time interval times a power coefficient and subtracting the flow during the time interval times a flow coefficient.

In step 760, the estimated eye temperature and the threshold temperature are compared. The amount of power delivered to the cutting tip 113 of the ultrasound handpiece 112 is adjusted, as necessary, in step 770, based on whether the estimated temperature exceeds the threshold or exceeds the threshold by a predetermined amount. For example, the power delivered to the handpiece may be reduced by reducing amplitude of the ultrasound signal and/or decreasing duty cycle of the ultrasound signal and/or or by enabling torsional vibration of the tip, if the estimated temperature exceeds the threshold, whereas the power may be maintained or increased if the estimated temperature is below the threshold.

Figure 8A:
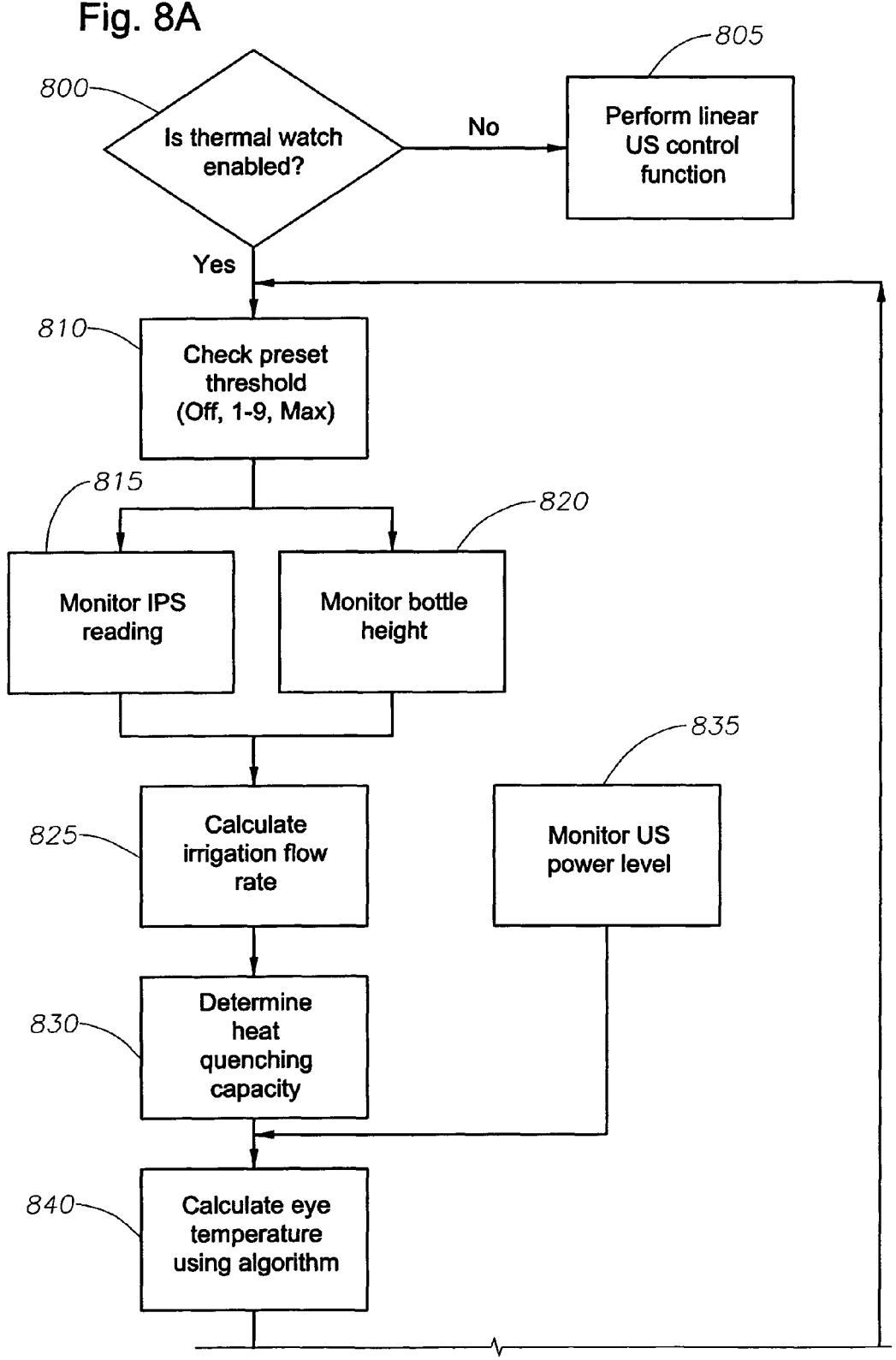
FIG. 8 is a more detailed flow diagram of one implementation of the embodiment shown in FIG. 7.
Figure 8B:
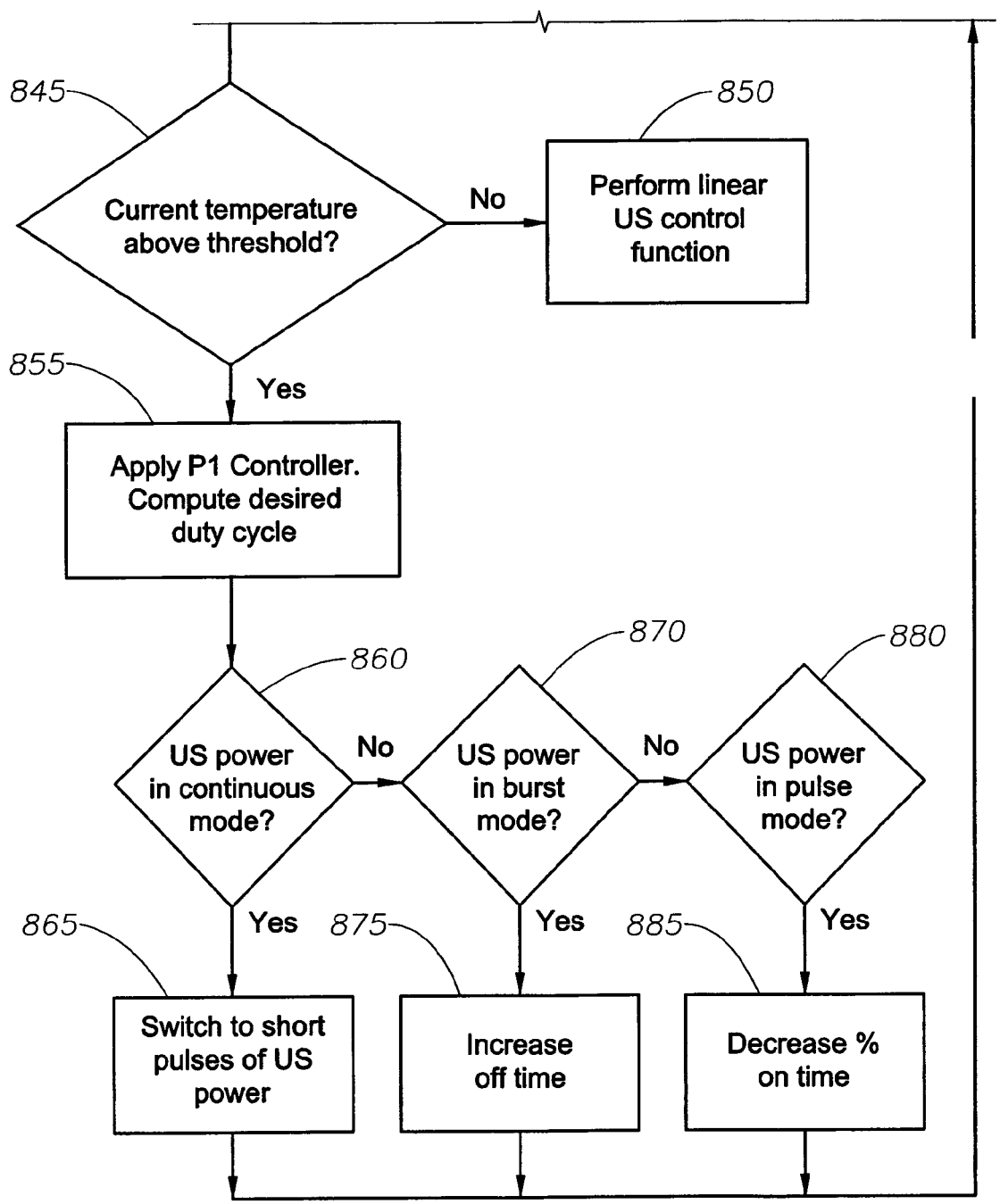

FIG. 8 illustrates one implementation of the process shown in FIG. 7. Referring to FIG. 8, in step 800, a determination is made whether the Thermal Watch™ feature is enabled. If Thermal Watch™ is not enabled, then in step 805, the system operates using linear ultrasound control functions. In other words, the ultrasound power delivered is controlled by the console settings and the surgeon's depression of the foot pedal.

If Thermal Watch™ is enabled, then in step 810, a threshold value, set by the surgeon, is noted or read by the system. The threshold value may be unitless and be in any number of steps from "Off" to "Maximum".

In step 815, the system monitors the pressure of the irrigation fluid (the "IPS Reading") and/or the height of the irrigation fluid source bottle 126 in step 820. These irrigation fluid pressure parameters, indicate the rate of flow of irrigation fluid, i.e., the quantity of irrigation fluid over a certain time, in step 825. Knowing the rate of irrigation fluid flow, the heat quenching capacity for that rate of irrigation fluid flow can be approximated (step 830). The flow function in time F(t) can approximate a linear function of pressure drop across the fluidics line: $F(t)=R(P_0-P(t))$, where $P_0$ is the irrigation source pressure (e.g. irrigation bottle height), P(t) is irrigation pressure sensor reading, and R is fluidic line resistance between the pressure source and the irrigation pressure sensor. The resistance R is established empirically for a given fluidic (i.e. consumable) configuration. The above approximation yields accurate results for a steady state flow conditions. To improve estimation accuracy for transient response an exponentially decaying correction can by added to the equation above as follows:

$$F(t) = R\left[(1+\delta)(P_0 - P(t)) - \delta\frac{1}{\tau_0}\int_{-\infty}^{t} e^{-\frac{\tau}{\tau_0}}(P_0 - P(\tau))d\tau\right]$$

where $\delta$ is the transient coefficient, and $\tau_0$ is the time constant of the approximated fluidic line. Both values can be established empirically for a given fluidic (i.e. consumable configuration). Sample values established for the Alcon INFINITI® system consumable are: $\delta=0.3$, $\tau_0=1.3$ seconds. The equation above can easily converted into a discrete form allowing practical implementation of the method.

The amount of heat that is generated by the ultrasonic cutting tip 113 of the handpiece 112 (i.e., the Ultrasonic or "US Power Level") is also monitored in step 835. The approximation of the heat quenching capacity for the irrigation fluid flow is then compared to the amount of heat that is generated by the ultrasonic cutting tip 113 to determine an approximate temperature of the eye in step 840. A determination is made whether the temperature of the eye is higher than a preset threshold value or is within a certain margin of the threshold in step 845. For example, the margin may be three degrees Fahrenheit (3° F.) within (e.g. below) the threshold, as shown in FIG. 8. Persons skilled in the art will appreciate that other pre-determined amounts or margins can also be utilized depending on the desired sensitivity of the system.

If the temperature of the eye is not within the margin (e.g. 3° F.) or does not exceed the threshold, then linear ultrasound control functions can be used (step 850). However, if the temperature of the eye is within the margin or exceeds the threshold, then the system utilizes an algorithm to compute an appropriate duty cycle in step 855. The control algorithm may be, for example, a standard linear control algorithm such as a PI (proportional-integral) or PID (proportional-integral-derivative) control algorithm. The control algorithm may also be a non-linear control algorithm, such as a bang-bang controller with or without hysteresis. Persons skilled in the art will appreciate that various algorithms can be used in different applications.

For example, in step 860, a determination is initially made whether the system currently operates in a continuous mode. In continuous mode, a continuous supply of power is applied to the handpiece without interruption. If the system is in continuous mode then in step 865, the system switches the mode of operation from continuous to pulsed ultrasonic power. If the system is not in continuous mode, then a determination is made in step 870 whether the system is operating in burst or pulse mode.

Figure 9:
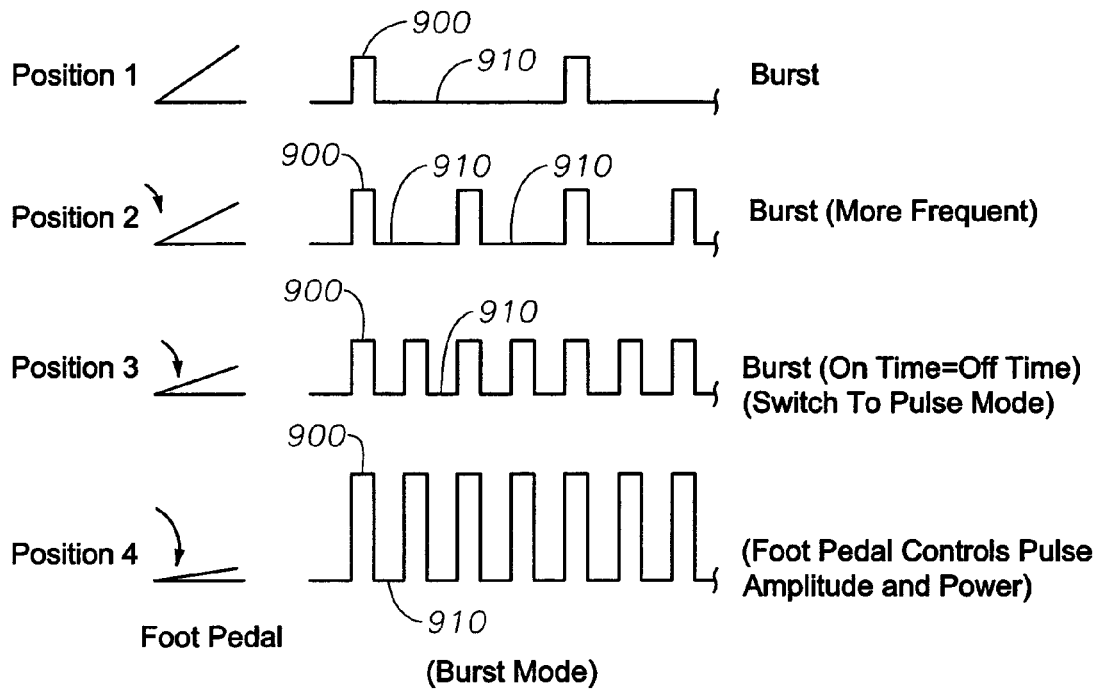
FIG. 9 illustrates exemplary burst mode pulses having constant amplitudes and different off times, and different off times being controlled by depression of a foot pedal.

Referring to FIG. 9a, burst mode provides a series of periodic, fixed width, constant amplitude pulses 900 of ultrasound power, each of which is followed by an "off" time 910. Persons skilled in the art will appreciate that in practice, the pulses shown in FIG. 9a and other figures are not "perfect" pulses. Rather, the pulses transition or ramp between different states due to, for example, capacitance and inductance. Thus, the ideal or model rectangular pulses shown in FIG. 9a and other figures are provided for purposes of explanation and illustration when, in practice, the pulses do not have a perfect rectangular shape.

The off time 910 between fixed width pulses 900 is controlled by the surgeon's input via, for example, depression of the foot pedal. In other words, in Burst mode, each pulse 900 has a fixed "on" time, and a variable "off" time. The "off" time is varied by adjusting the position of the foot pedal or foot switch.

For example, FIG. 9a illustrates a foot switch in four positions: The off time 910 decreases when the foot pedal is initially at Position 1 and depressed further to Position 2, and decreases further when the foot pedal is depressed from Position 2 to Position 3. Thus, the number of fixed width, constant amplitude pulses in a period of time increase as the foot pedal is depressed further. As the foot pedal is depressed further, the off time eventually equals the on time. In this case, further depression of the foot pedal from position 3 to position 4 results in the amplitude of the pulses being increased, while maintaining the same off time 910. In other words, pulse amplitude can be made after the off time is the same as the on time, thereby increasing power delivered to the handpiece.

Referring again to FIGS. 8 and 9a, if the system is in burst mode, a number of pulses of ultrasound power having the same pulse width can be adjusted in step 875 by decreasing the power "On" time or increasing the power "Off" time, thereby providing fewer fixed width pulses in a given time and less power to the ultrasonic tip 113, in order to cool the tip 113. If the system is not in burst mode, in step 880, the system is in a pulse mode.

Figure 10:
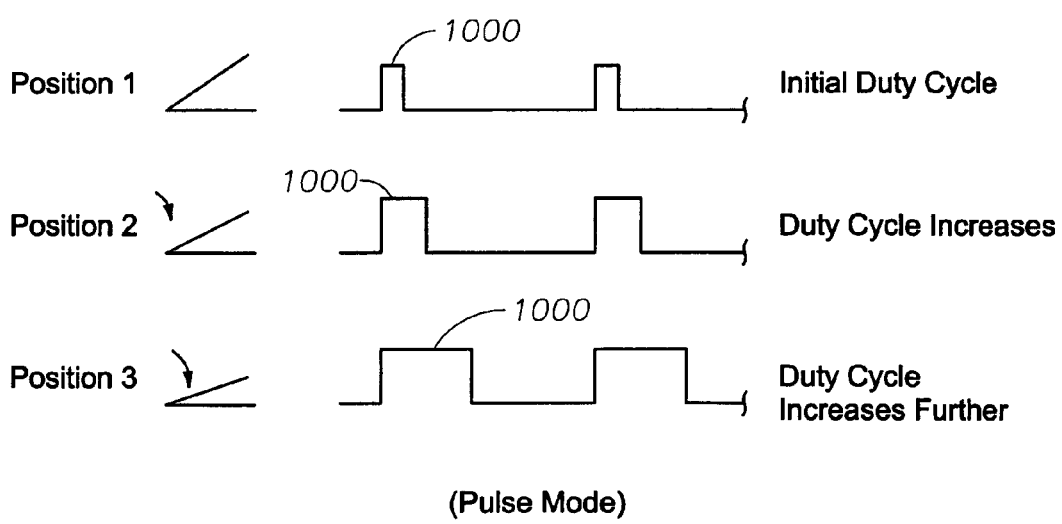
FIG. 10 illustrates exemplary pulse mode pulses having different duty cycles, and duty cycles being controlled by depression of a foot pedal.

Referring to FIGS. 8 and 10, if the system is in pulse mode, then the amplitude of the pulses 1000 remains constant, and the power delivered to the handpiece can be adjusted in step 885 by adjusting the duty cycle of the power pulses being supplied to handpiece 112. In an ideal train of rectangular pulses 1000, the ratio of the pulse duration to the pulse period or the ratio of the duration of the "high" pulse level to the sum of the durations of the "high" and "low" levels (one period) is the duty cycle, represented as a fraction or percentage. Thus, the duration of each constant amplitude pulse 1000 can be changed (e.g., become narrower or wider) to change the duty cycle, and thus change the amount of power that is delivered to the handpiece.

Alternatively, if the system is operating in continuous mode (860), and the temperature of the eye is above the threshold, then the power can be switched off until the eye temperature drops below the threshold. Further, if the system is operating in a burst or pulse mode and temperature of the eye is above the threshold, power can be turned off for a remainder of a pulse, and the next power pulse can be delayed, if necessary, until the eye temperature drops below the threshold. Further, if the temperature of the eye is above the threshold, then the power level (stroke length) can be reduced to help prevent injury to the eye rather than manipulation of the pulse duty cycle.

Persons skilled in the art will appreciate that the Thermal Watch feature can be used with different types of pulses, e.g., continuous, pulsed, burst, and pulses having different patterns, such as pulses described later in this specification and shown in FIGS. 14-24 since Thermal Watch serves as a governor that periodically determines the amount of power delivered, regardless of the type of pulse or pulse pattern, and how that determined amount of power compares to the threshold and how the amount of power compares to the threshold, as previously described.

Similar power adjustments can be made when an occlusion event is detected. For example, in one embodiment, the power delivered to the tip 113 can be increased by increasing the "On" time or by decreasing the power "Off" time in the ultrasound duty cycle so as to increase the cutting efficiency of handpiece 112. The temperature of eye can be monitored using the Thermal Watch™ feature to decrease the power "On" time, or increase the power "Off" time prior to tip 113 becoming overheated. Accordingly, embodiments provide a manner of effectively increasing power when necessary (e.g., when an occlusion event occurs), but effectively monitoring and reducing the power, as necessary, in order to prevent overheating of the tip 113 and burning or damaging eye tissue.

An alternative embodiment is directed to a load detection system and method, generally referred to as "Power on Demand," can limit or overrule the amount of power that is requested by a surgeon if it is determined that too much power is being requested in order to prevent damage to eye tissue. The system can detect when the cutting tip 113 is no longer in contact with lens tissue or is in contact with different sections of a lens tissue with varying hardness, and automatically adjusts the amount of power delivered to the handpiece.

As previously discussed, one or more piezoelectric crystals in the handpiece 112 are driven by power that is provided by a power supply. The crystals vibrate, which in turn causes a needle in the handpiece to vibrate and emit ultrasound energy. The surgeon positions the needle so that the ultrasound energy is delivered to an eye tissue, such as a lens to, for example, break up cataracts. A separate aspiration system is used to remove tissue fragments. A surgeon may request that a certain amount of power be delivered to the tip 113, by, for example, depressing a foot switch or other switch activator. During the surgical procedure, the system applies a low level of voltage to the crystals causing them to emit a small amount of ultrasound energy. The voltage across the crystals and the current through the crystals under this condition are then measured. The voltage and current values are used to calculate a power value that is drawn by the handpiece. The ultrasound handpiece 112 tends to draw more power in order to maintain a given stroke (amplitude) when the tip 113 is in contact with harder tissue or material (such as a cataractuous lens). This increase in power based on contact with material encountered by the tip in a typical cataract surgery has been found to be measurable at lower power settings. In a modified pulsed mode, a small amount of power is applied to the tip 112 between the higher power pulses used to cut the tissue. In other words, a small amount of power is applied during low power periods.

Figure 11:
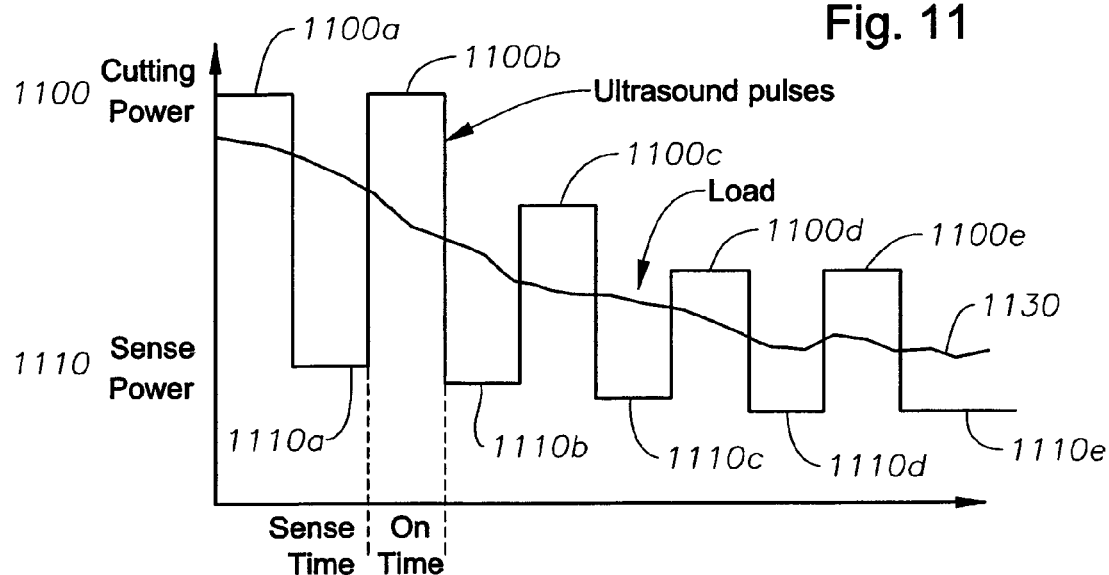
FIG. 11 illustrates non-zero Sense Power levels between cutting pulses according to one embodiment.

For example, as shown in FIG. 11, the pulsed mode type driving signal includes alternating intervals of high or cutting power 1100 a-e (generally 1100) and alternating intervals of low or sense power 1110 a-e (generally 1110) between the cutting intervals 1100. The amplitude of the sense interval 1110, however, is greater than zero. In other words, the sense power does not decrease to zero following a cutting interval.

In the illustrated embodiment, the duration of the cutting interval 1100 and sense interval 1110 are approximately the same. Voltage and current measurements are performed during the sense intervals in order to correlate an amount of power that is drawn by the handpiece 112 during the sense interval, with a load 1130 at the tip 113. Some degree of cutting may also occur since a small amount of power is still applied to the tip, however, cutting primarily occurs during the higher power cutting interval. Thus, although this specification refers to a "sense" interval, both sensing and cutting may occur during this interval.

The amount of power drawn by a handpiece 112 is determined during the sense interval 1110 is then used to adjust the power of the next or subsequent cutting interval 1100. The power is adjusted proportionately based on the detected power and the surgeon's request. In other words, if a higher load is detected at the tip, a higher in portion (possibly all) of the power requested by a surgeon will be delivered on the next cutting interval. Likewise, if a lower load is detected, a smaller portion (possibly none) of the power requested by the surgeon will be delivered during the next cutting interval 1110.

For example, the power detected during sense interval 1110a is used to proportionately adjust the power level of the next cutting interval 1100b. Similarly, the power detected during sense interval 1110b is used to proportionately adjust the next cutting interval 1100c. Thus, the cutting power 1100 is continuously adjusted to compensate for different loads 1130 on the ultrasonic tip 113 of the handpiece 112.

As shown in FIG. 11, the power level of the sense interval 1110 is relatively constant over time. The sense interval 1110, however, may vary, but should not be zero or so low that a load at the tip cannot be detected. The power level of the sense interval 1110 can vary depending on, for example, system parameters and the sensitivity of measuring equipment. Accordingly, embodiments using non-zero sense periods are in contrast to known "pulse mode" driving systems that typically use alternating high power and zero power pulses, i.e., switching between "on" and "off" rather than switching between high power and low power or "on" and "low power."

Due to the variation in ultrasound handpieces and cutting tips, the load 1130 sensing feature should be calibrated at the beginning of each surgery. For example, calibration can be performed during a "tune cycle" during which the handpiece tip 113 is placed in a test chamber filled with irrigation fluid. At this time, ultrasound power is applied to the tip 113 at the sensing power setting. The amount of power drawn by the handpiece 112 under this baseline condition is saved in the control system memory as a threshold or a "no-load" condition. If necessary, as surgery progresses, the control system 114 may use automatic threshold adjustment to adjust this threshold value based on loads 1130 that are measured during the surgery.

The load sensing feature also allows the surgeon to control the sensitivity of the adjustments made by the control system 114. More specifically, a sensitivity adjustment is a linear or coefficient adjustment that sets the gain of the power reductions made when less than full load is sensed. Once the threshold and sensitivity are set, the power to the handpiece 112 may be adjusted based on an algorithm.

Figure 12:
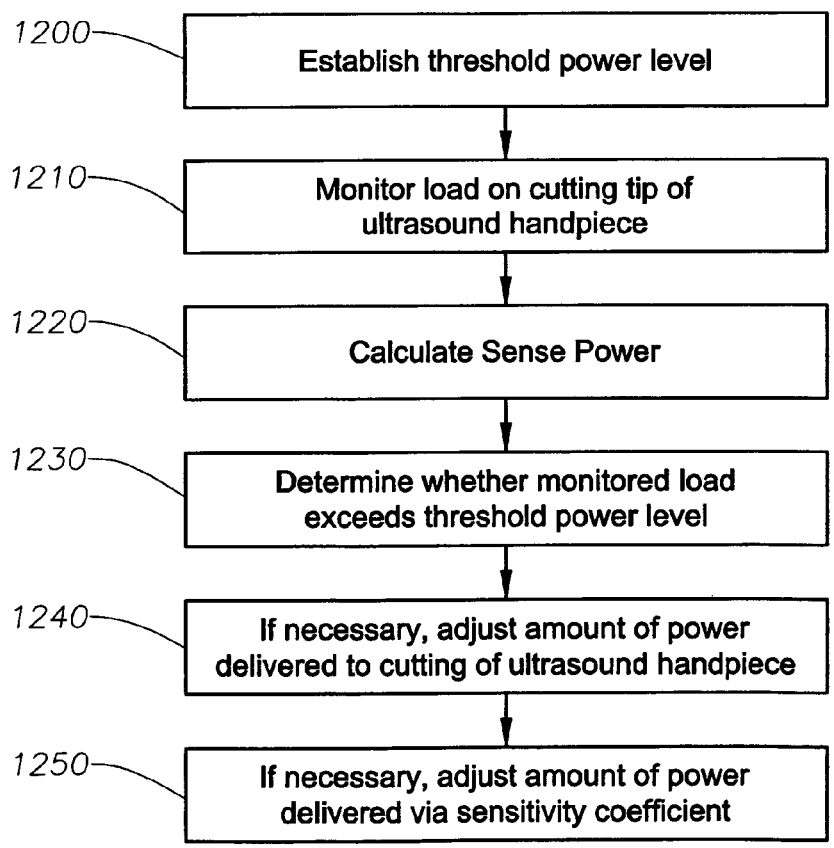
FIG. 12 flow diagram illustrating a method for adjusting power based on power, threshold and sensitivity calculations.
Figure 13:
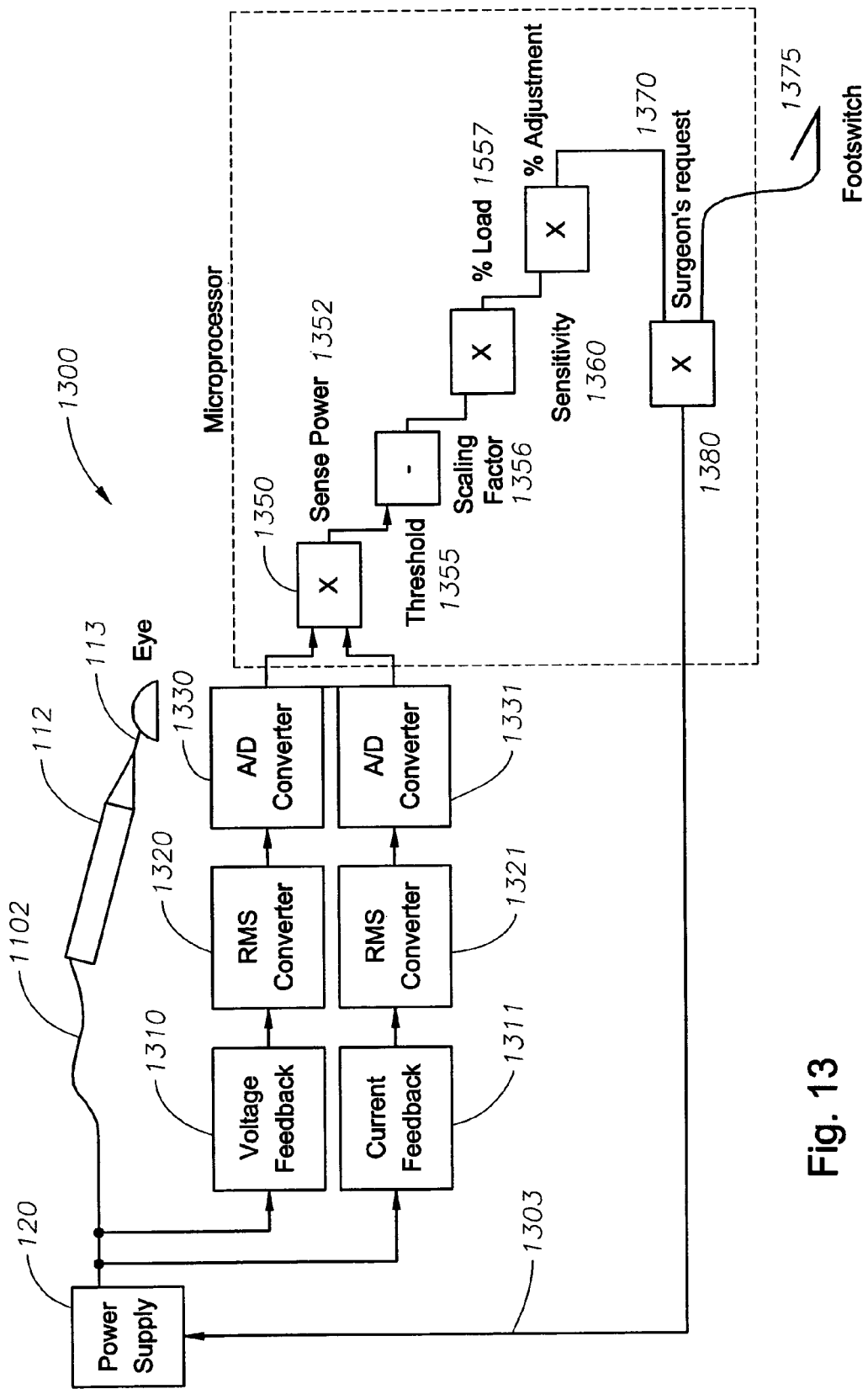
FIG. 13 is a schematic of handpiece power supply system that may be used with one embodiment.

FIGS. 12 and 13 illustrate one embodiment of an algorithm and system that operates based on the algorithm for performing these power stroke or amplitude variations based on the sensed voltage and current load 1130. Initially, a threshold value 1355 is determined in step 1200. As previously discussed, the threshold power 1355 is a fixed value that is determined after operating the ultrasonic handpiece 112 in an irrigation solution or saline or other reference environment. In other words, the threshold power 1355 represents a baseline power when no tissue is being cut.

The power drawn by the cutting tip 113 is monitored in step 1210. A power supply 120 is coupled to the handpiece 112 and delivers power to the tip 113 via a power line 1302. A power control system 1300 is connected to the inputs and outputs of the power supply 120 via connectors 1303-1305. The connectors 1304 and 1305 are coupled to the output of the power supply 120, and the connector 1303 is coupled to the input of the power supply 120.

The power control system 1300 shown includes feedbacks 1310 and 1311 for voltage and current. The feedback components 1310 and 1311 are coupled to the connectors 1304 and 1305. Voltage and current measurements obtained during sense intervals 1110 are based on the stresses placed on the piezoelectric crystals in the handpiece 112. If the needle or tip 113 encounters tissue that is more resistant to cutting (a high load), the magnitudes of the voltage and/or the current may increase, whereas if the needle or tip 113 encounters tissue that is more easily cut (a lower load), the magnitudes of the voltage and/or current may decrease. The voltage and current values obtained by the feedbacks 1310 and 1311 during each sense interval 1110 are provided to respective Root Mean Square ("RMS") converters 1320 and 1321.

The RMS converters 1320 and 1321 determine an average voltage magnitude and an average current magnitude over a defined period of time. These RMS values are provided to Analog to Digital ("A/D") converters 1330 and 1331, which provide digital signals representing the respective measured analog voltage and current to a microprocessor 1340.

The microprocessor 1340 can be the same microprocessor 116 as discussed above or a separate microprocessor or controller. The digital voltage and current values are provided by the A/D converters 1330 and 1331 to the microprocessor 1340. Software in the microprocessor 1340 calculates 1350 the "Sense" power 1352 detected during a sense interval 1110 as Power ("P")=Voltage ("V")×Current ("I") based on the values provided by the A/D converters 1330 and 1331. Thus, the calculation involves a linear calculation without the necessity to account for non-linear attributes, such as phase and resonance. The sense power 1352 is then compared to the threshold or baseline power 1355.

The calculated sense power 1352 exceeds the threshold or base power 1355 when power is needed by the handpiece 112 to cut tissue, i.e., when the handpiece 112 is applied to something other than the base material or liquid, such as saline. The comparison of sense power 1352 and the threshold power 1355 is used to determine how the power to be delivered to the handpiece 112 should be adjusted, if at all, during the next cutting interval in step 1240 based on the characteristics of the tissue encountered by the tip 113 of the handpiece 112. This comparison is multiplied by a scaling coefficient 1356 that is stored in the handpiece or in the software that relates the amount by which the sense power 1352 exceeds the threshold power 1355 to the fraction of full loading detected 1357. The scaling coefficient 1356 can, for example, be empirically determined based on prior operation of the system.

In addition to this threshold comparison and percent load calculation, a sensitivity adjustment or coefficient 1360 is set by the surgeon to indicate what fraction of the power requested by the surgeon should be delivered to the tip during the next cutting interval based on an amount by which the sense power 1352 exceeds the threshold power 1355. The sensitivity coefficient 1360 ranges from 0-1 or is otherwise generally represented as a % value, e.g., 20%, 50% or 85%. These values may be represented to the surgeon as off, low, medium, high or some other scale or indication. In step 1250, values obtained by the (sense voltage−threshold)×scaling factor calculation are multiplied by the sensitivity coefficient 1360. A greater quantity of the requested power 1370 (e.g., as indicated by the level of a footswitch 1375) is delivered to the handpiece 112 with higher sensitivity coefficients than with lower sensitivity coefficients. For example, if the surgeon requests "X" amount of power 1370 via the foot pedal 1375, then some, all, or none of that "X" power 1370 may be delivered to the handpiece 112 depending on the sensitivity coefficient 1360.

Thus, the power 1380 that is actually delivered to the handpiece 112 may be less than or the same as the amount of power requested 1370 by a surgeon by depression of the foot pedal 1375. Accordingly, the embodiments use linear relationships and calculations, threshold determinations and linear calculations based on sensitivity coefficients in order to adjust the amount of power 1380 that is delivered to a handpiece 112.

FIG. 11 illustrates one pulse pattern that includes cutting and sense intervals for use with the Power on Demand system shown in FIGS. 12 and 13. The pulse pattern shown in FIG. 11 includes cutting and sense intervals that are relatively constant and approximately the same duration. In alternative embodiments, different pulse patterns may be used with different cutting and sense intervals, as shown in FIGS. 14-24. In order to illustrate the different cutting and sensing pulses and intervals, the pulses are shown without a corresponding load, however, persons skilled in the art will appreciate that the amplitudes of the cutting intervals may be adjusted as necessary depending on the load at the tip of the handpiece. This specification refers to an "interval" and a "pulse". A pulse is a signal that begins from and ends at zero power, whereas an interval can be considered to be part of a pulse and thus, either begins or ends at zero power. However, for purposes of this specification, these terms are interchangeable since they both provide durations of sense power and durations of cutting power. Accordingly, "interval" is intended to include a "pulse" and a "pulse" is intended to include an "interval".

Figure 14:
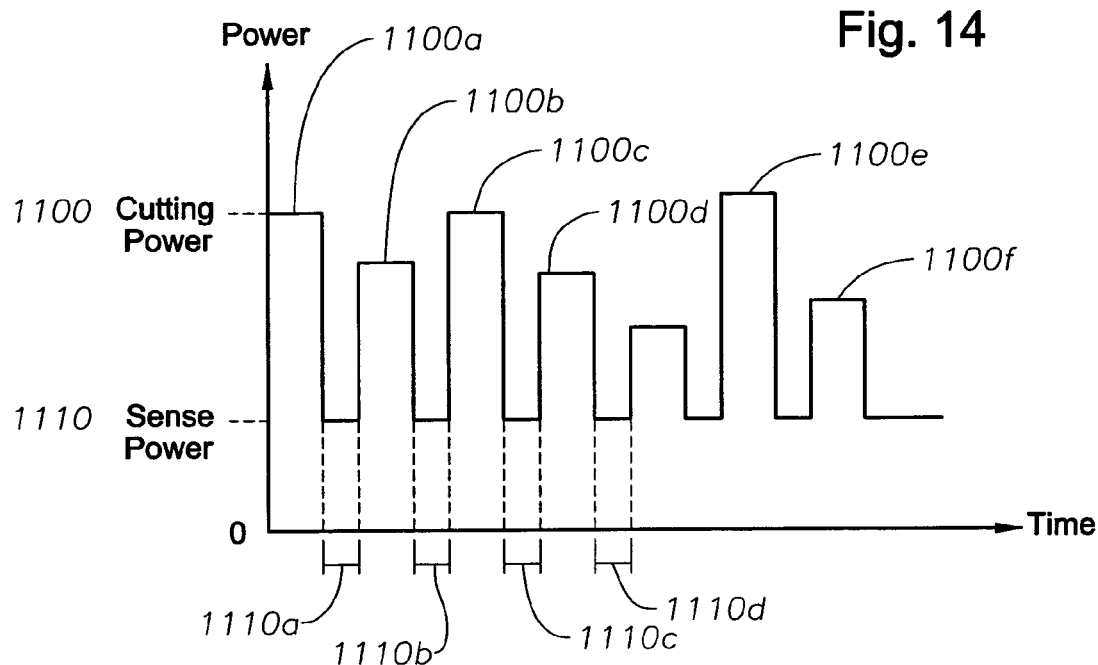
FIG. 14 illustrates non-zero Sense Power levels having durations that are shorter than the Sense Power level durations shown in FIG. 11 according to a further embodiment.
Figure 15:
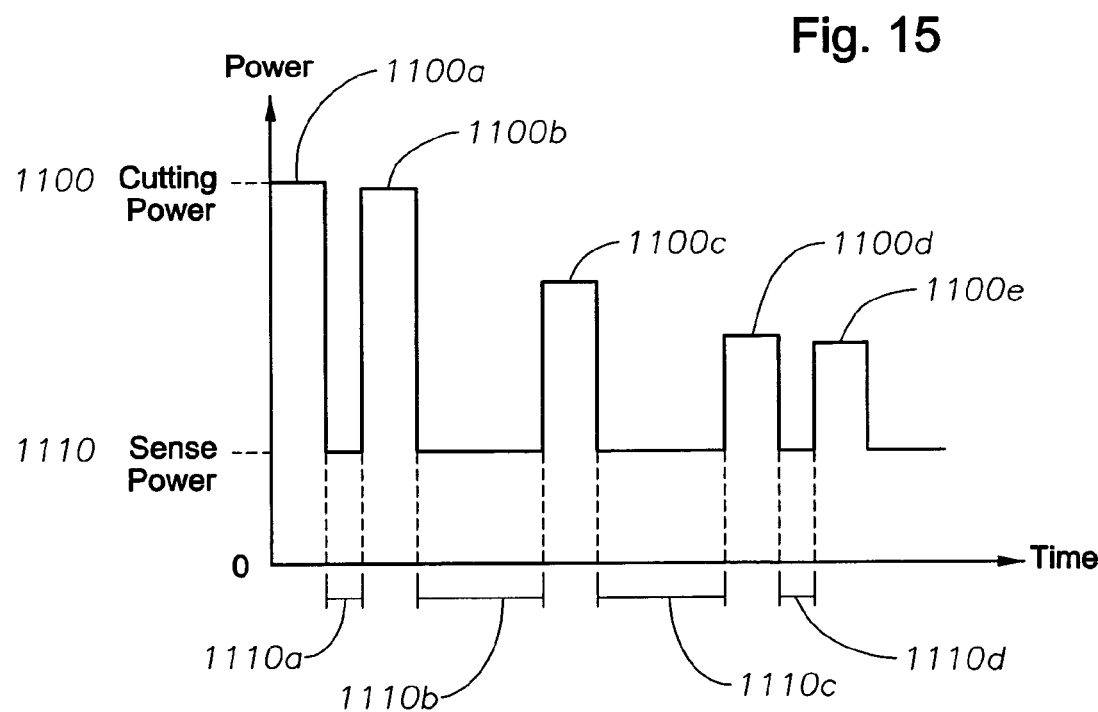
FIG. 15 illustrates non-zero Sense Power levels between cutting levels and that have durations that vary over time according to a further embodiment.

Referring to FIG. 14, in an alternative embodiment, the durations of the sense intervals 1110 are approximately the same over time and shorter than the durations of the cutting intervals 1100. In a further embodiment, shown in FIG. 15, the duration of the sense intervals 1110 can vary over time so that they are shorter than, about the same duration as, or longer than the cutting intervals. The duration of sense intervals 1110 can be adjusted to accommodate, for example, Signal to Noise (S/N) ratios and system response. A longer sense interval 1110 may provide better S/N ratios and a more delayed response. Thus, the duration of sense intervals 1110 can be selected to coordinate with system components and capabilities.

Figure 16:
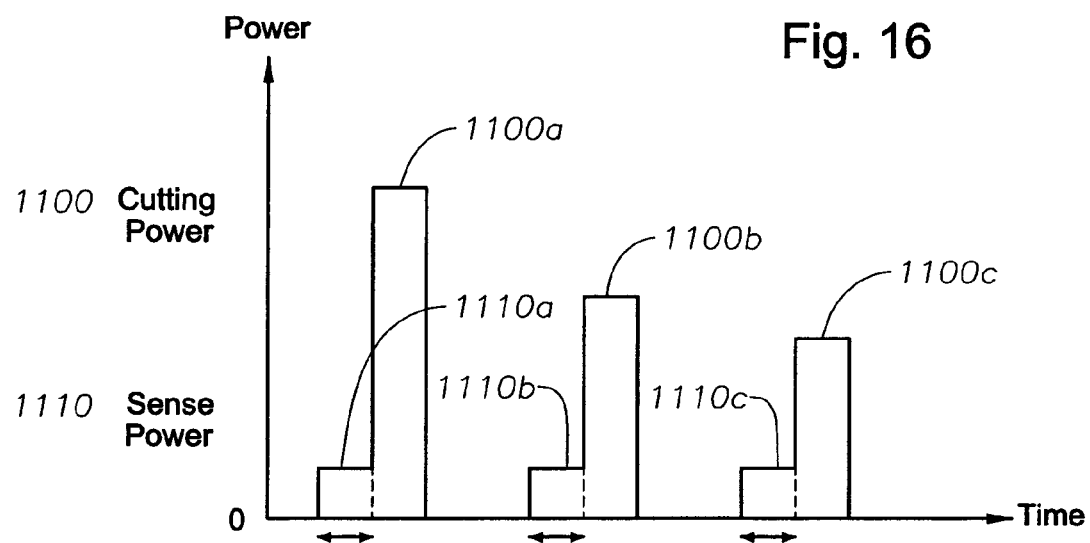
FIG. 16 illustrates separate non-zero Sense Power pulses between cutting pulses and power being zero between the cutting and Sense Power pulses according to another embodiment.
Figure 17:
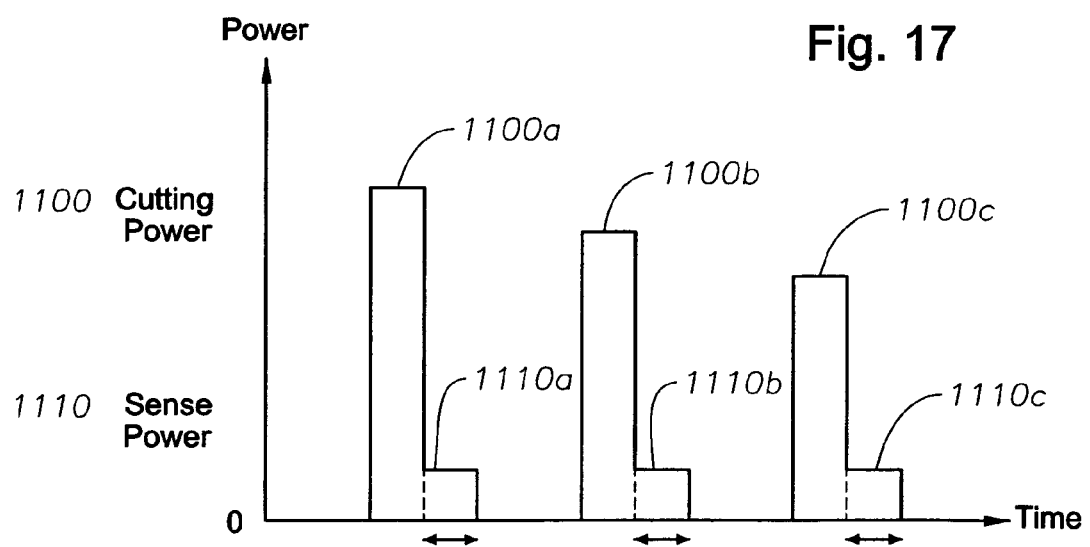
FIG. 17 illustrates separate Sense Power pulses between cutting pulses and the duration of the Sense Power pulses being shorter than the duration of the Sense Power pulses shown in FIG. 16 according to a further embodiment.

Referring to FIG. 16, in a further alternative embodiment, the sense interval 1110 can immediately precede separate cutting interval 1100. For example, power increases from a zero level to a low power level during the sense interval 1110. Immediately following the sense interval 1100 is the cutting interval 1100. The cutting interval 1100 is at a higher power level than the sense interval 1110. After the cutting interval 1100, the power returns to zero, and the interval sequence can be repeated. FIG. 17 illustrates a similar configuration except that the high power cutting pulse 1100 immediately follows a period of zero power. The sense interval 1110 immediately follows the higher power cutting interval 1100 and then followed by zero power, which can be repeated as necessary.

Figure 18:
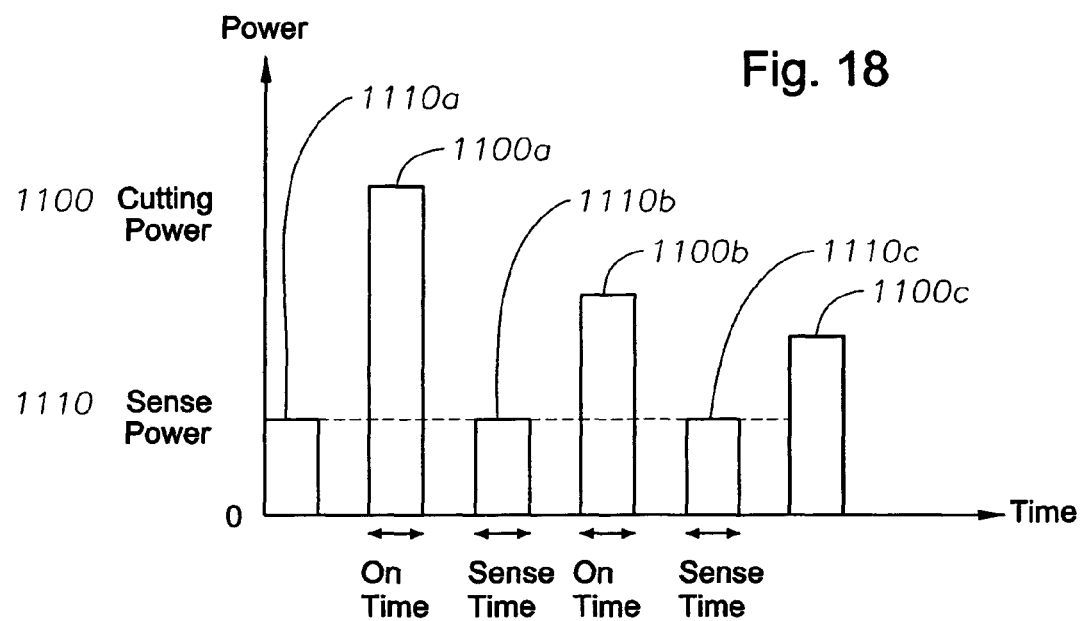
FIG. 18 illustrates separate non-zero Sense Power pulses having durations that vary over time according to another embodiment.
Figure 19:
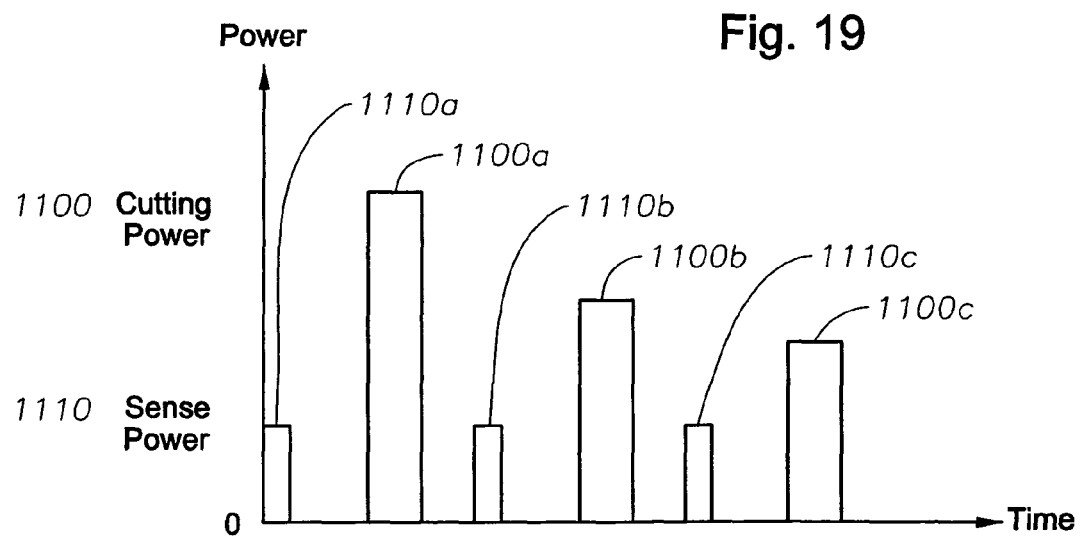
FIG. 19 illustrates non-zero Sense Power pulses immediately prior to cutting pulses according to another embodiment.
Figure 20:
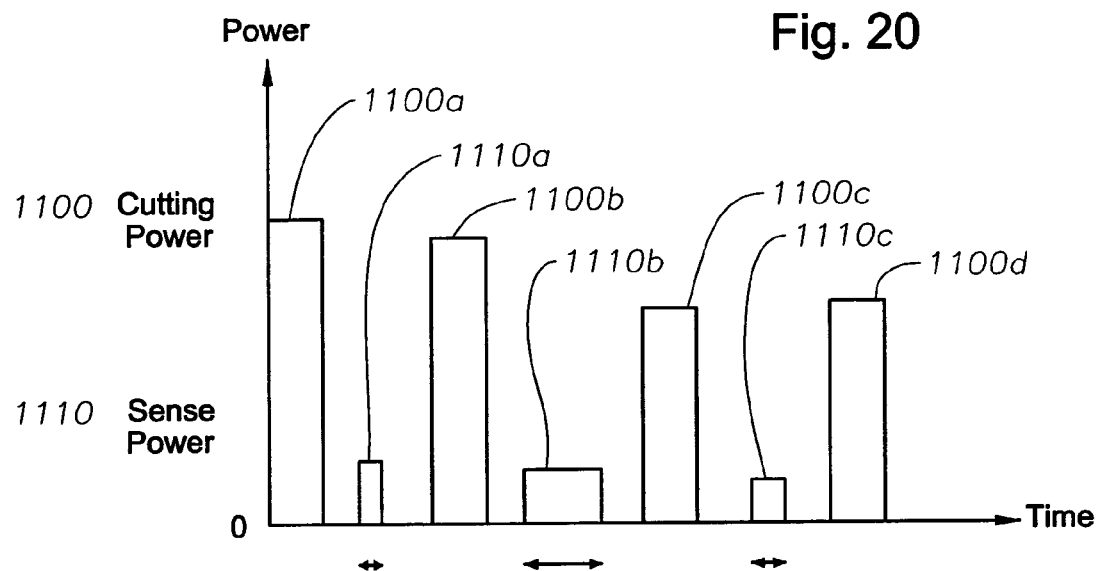
FIG. 20 illustrates non-zero Sense Power pulses immediately following cutting pulses according to another embodiment.

FIG. 18 illustrates another embodiment in which a separate low power, sense pulses 110 are triggered between separate higher power cutting pulses 1100. In the illustrated embodiment, the cutting and sense pulses 1100 and 1110 have about the same duration. FIG. 19 illustrates another alternative embodiment that utilizes separate sense pulses 1110 and cutting pulses 1100, and in which the duration of the sense pulse 1110 is shorter than the duration of the cutting pulse 1100. FIG. 20 illustrates a further embodiment in which separate sense pulses 1110 have varying durations and are between cutting pulses 1100.

Figure 21:
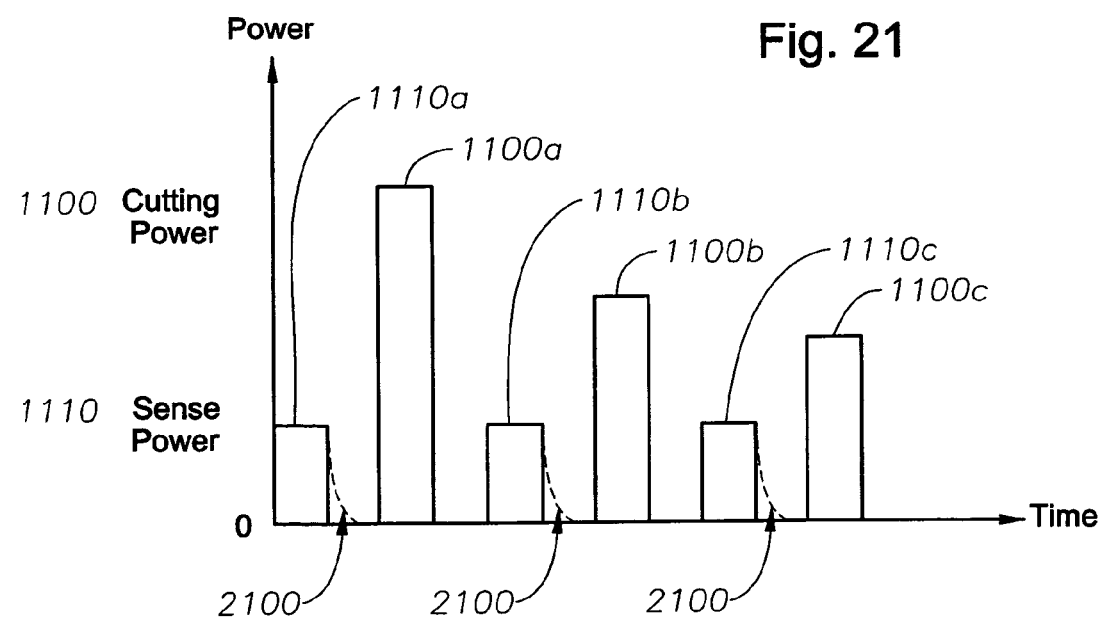
FIG. 21 illustrates separate Sense Power pulses between cutting pulses and Sense Power measurements being made based on a decaying Sense Power pulse according to another embodiment.
Figure 22:
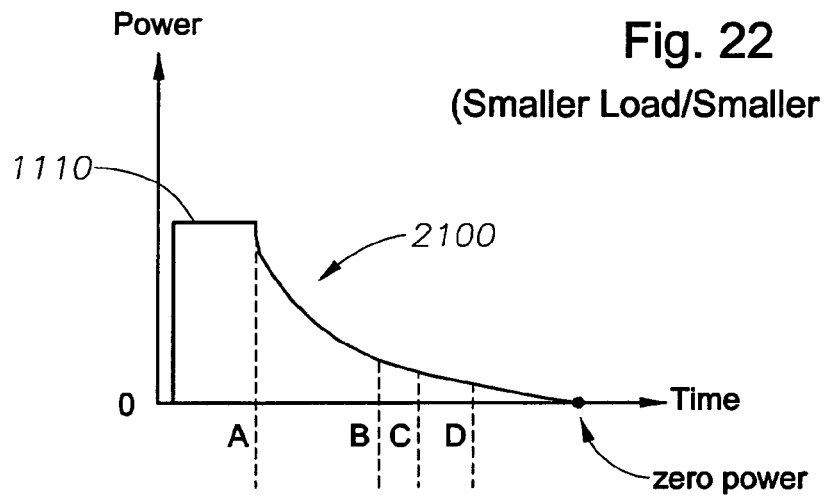
FIG. 22 illustrates measurements taken with respect to a slower decaying Sense Power pulse.
Figure 23:
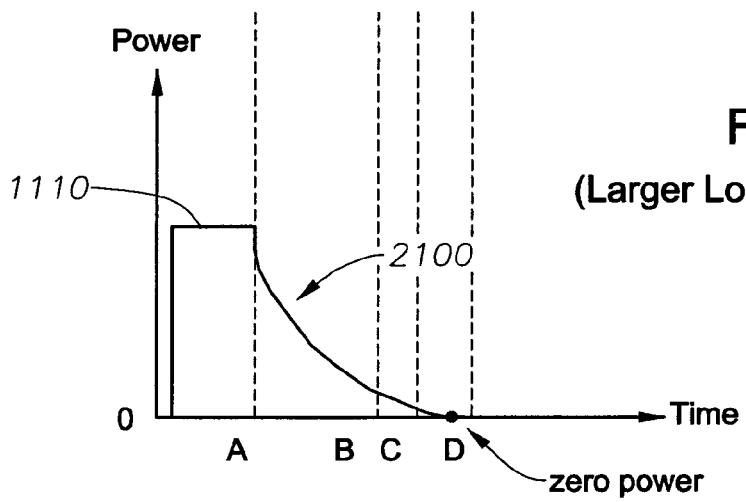
FIG. 23 illustrates measurements taken with respect to a faster decaying Sense Power pulse.

FIG. 21 illustrates yet a further alternative embodiment that includes separate sense pulses 1110 and cutting pulses 1100, and where the voltage and current data are obtained during the decay 2100 of a sense pulse 1110. This embodiment is illustrated in further detail in FIGS. 22 and 23. Rather than determining the load as shown in FIG. 11, the system can be configured to determine the time that it takes for a sense interval pulse 1110 to decay to a certain level. The rate of decay can be affected by the load on the tip. For example, a larger load will cause the sense pulse to decay more quickly, whereas a smaller load will result in the sense pulse decaying more slowly. FIG. 22 shows a sense pulse taking longer to decay due to a smaller load, and FIG. 23 illustrates a sense pulse decaying more quickly, due to a larger load. This decay technique can also be applied to other pulse patterns, including sense intervals that immediately follow a cutting interval, such as sense intervals shown in FIG. 17.

The time required for a sense pulse or interval to decay to a certain level can be correlated to a load at the tip. This can be done using, for example, a lookup table that cross-references the rate of decay and a load at the tip. This decay and load information can then be used to adjust the power level of the next cutting pulse or interval if necessary. For example, referring to reference Point C in FIGS. 22 and 23, the rate of decay of the pulse shown in FIG. 23 is faster than the rate of decay of the pulse shown in FIG. 22. As a result, the amount of power delivered during the next cutting pulse following the sense pulse shown in FIG. 22 may be less than amount of power delivered during the next cutting pulse following the sense pulse shown in FIG. 23 since the pulse shown in FIG. 23 decays faster due to a larger load at the tip. The rate of decay analysis can be repeated to continuously adjust the power delivered to the tip during the next cutting pulse or interval According to a further embodiment, cutting and sense pulses can be at different frequencies. For example, cutting pulses can be applied at a particular frequency, and a sense pulses can be applied at one of the harmonics of the cutting pulse frequency. For example, cutting pulses may be applied at about 40 kHz, and sense pulses can be applied at one of the harmonics, such as 80 kHz or 120 kHz.

Persons skilled in the art will appreciate that the FIGS. 11 and 14-23 are provided as exemplary sense and cutting interval patterns and are not intended to be limiting since sense and cutting intervals can be adjusted as necessary for different systems and applications. Further, persons skilled in the art will appreciate that both sensing and some degree of cutting may occur during a lower power sense interval since sensing occurs at a non-zero level, and some cutting occurs, although the amount of cutting is small compared to cutting that occurs during a higher power cutting interval. Persons skilled in the art will also appreciate that the Thermal Watch feature can be used with these different pulse patterns since the Thermal Watch considers the amount of power delivered and is not dependent on a particular pulse pattern.

Figure 24:
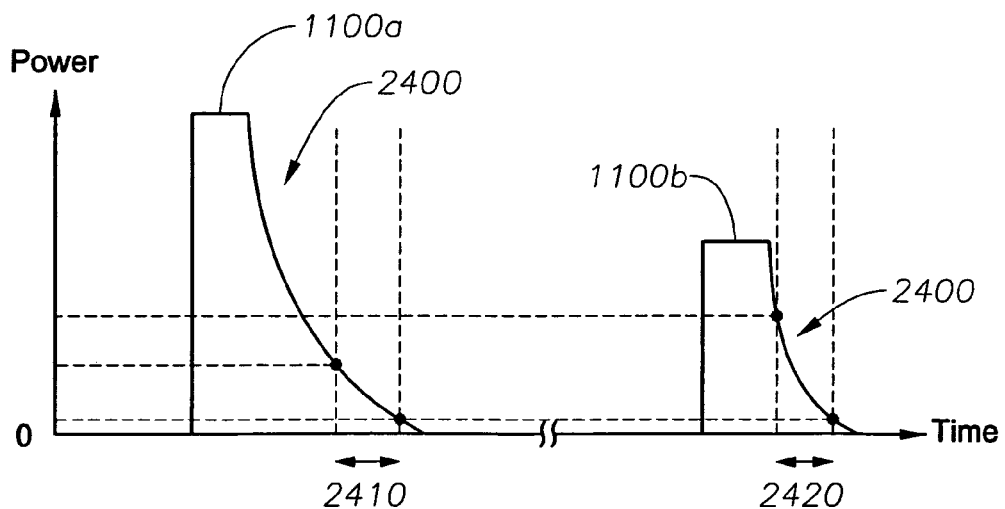
FIG. 24 illustrates Sense measurements being taken with respect to a rate of decay of a cutting pulse after the cutting pulse is switched from a high level to a low level according to another embodiment.

Referring to FIG. 24, in a further alternative embodiment, the rate of decay 2400 of a cutting pulse 1100 can be correlated to a load at the tip. Depending on the amplitude of the cutting pulse 1100, it may be desirable to sample the tail end 2410 of the decaying pulse 2400 since the power level of the decaying cutting pulse may be too high at the beginning of the decay period, thereby causing interference with the power and current measurements. The time required for a cutting pulse to decay to a certain level can be cross-referenced with a lookup table so that the rate of decay can be correlated to a load at the tip. This decay and load information can then be used to adjust the power level of the next cutting pulse if necessary.

One skilled in the art will recognize that torsional movement involves a twisting or rotation of the tip about the longitudinal axis of the tip. Such torsional movement may be accomplished by an ultrasonic handpiece having a programmable ultrasound driver capable of producing both a torsional frequency drive signal and a longitudinal frequency drive signal. Such handpieces are well-known to those in the art, with one example being described in U.S. Pat. No. 6,028,387 at column 2, line 6-67, column 3, lines 1-67 and FIGS. 2-3, such disclosure being incorporated herein by reference.

Figure 25:
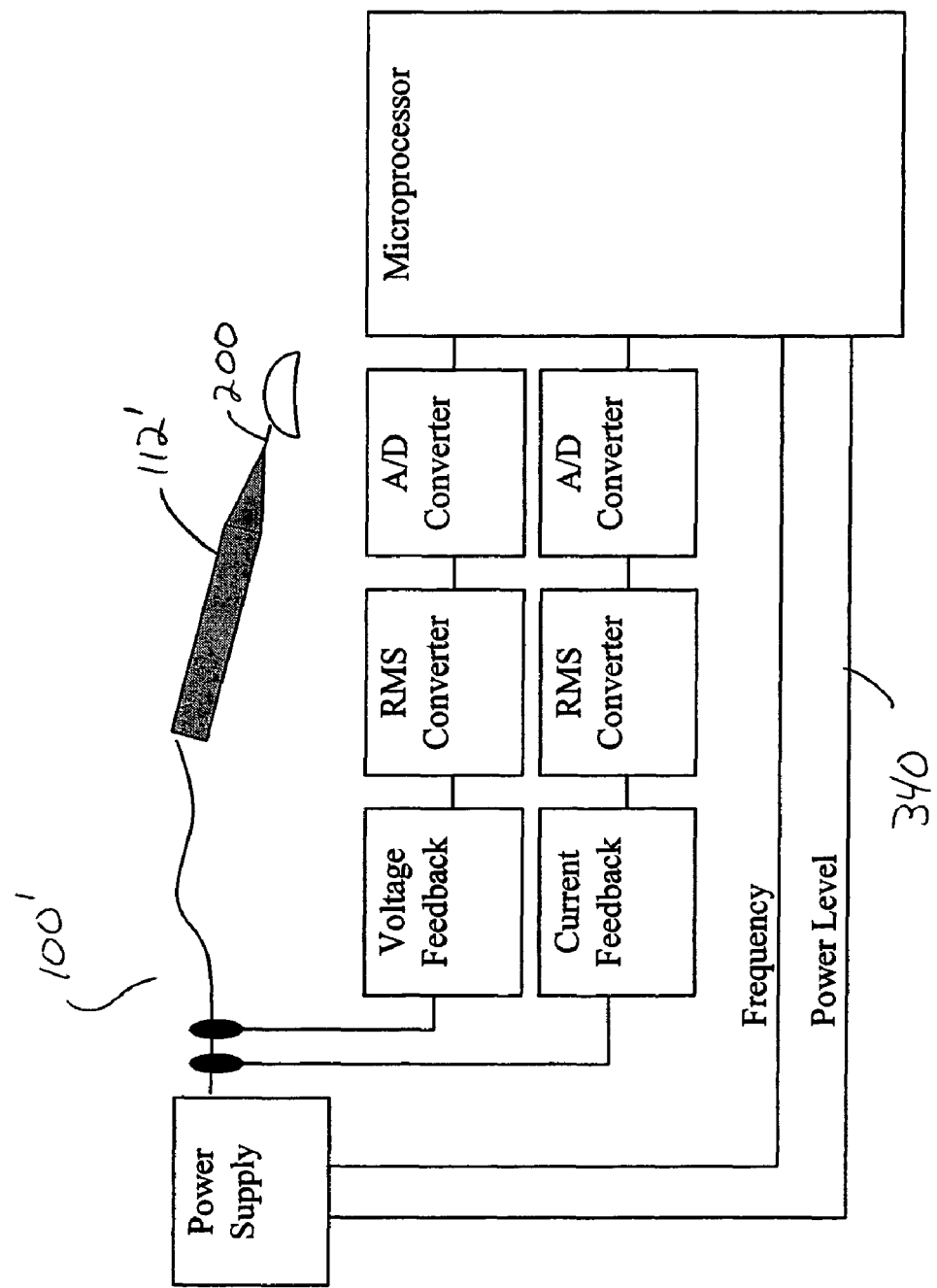
FIG. 25 is a block diagram of an alternative drive circuit that may be used with the present invention.

As best seen in FIG. 25, an alternative control system, 100' suitable for driving a torsional handpiece 112' contains drive circuit 340 and preferably is similar to that described in U.S. Pat. No. 5,431,664, the entire contents of which being incorporated herein by reference, in that drive circuit 340 tracks the admittance of handpiece 112' and controls the frequency of handpiece 112' to maintain a constant admittance. However, drive circuit 340 monitors both the torsional mode and the longitudinal mode and controls these modes in handpiece 112' using two different drive frequencies. Preferably, the torsional drive signal is approximately 32 kHz and the longitudinal drive signal is 44 kHz, but these frequencies will change depending upon the piezoelectric elements used and the size and shape of the horn (not shown). Although both the longitudinal or the torsional drive signal may be supplied in a continuous manner, preferably the longitudinal drive signal and the torsion drive signal are alternated, so that the drive signal is provided in a desired pulse at one frequency and then switched to the other frequency for a similar pulse, with no overlap between the two frequencies, but no gap or pause in the drive signal. Alternative, the drive signal can be operated in a similar manner as described, but short pauses or gaps in the drive signal can be introduced. In addition, the amplitude of the drive signal can be modulated and set independently for each frequency.

The pause or gap between drive signals can serve various purposes. One purpose is to allow for the ultrasound movement of the piezoelectric elements and the horn to attenuate or stop so that lens fragments can once again be suctioned to tip 200 and an occlusion reestablished, thereby increasing the holding force on the lens fragment. Reestablishing the occlusion will increase cutting efficiency of the following pulse of ultrasound, whether longitudinal or torsional. Another purpose of the pause or gap between drive signals is to allow for the ultrasound movement of the piezoelectric elements and the horn to attenuate or stop prior to the other (either longitudinal or torsional) mode being excited. Such attenuation between drive signals will reduce amount of potential nonlinear interactions in the system which can generate undesirable heat and lead to premature degradation of piezoelectric elements 14 or mechanical failure of the entire assembly.

Alternatively, there can be a slight overlap in the longitudinal and torsional drive signals. The overlap may provide relatively short time intervals when the added action of both torsional and longitudinal displacements results in especially fast rate of lens emulsification, and yet the overlap is short enough to prevent the piezoelectric elements from premature degradation or failure of the entire mechanical assembly as a result of excessive stress.

Yet another alternative if to have both longitudinal and torsional drive signals overlap completely thus resulting in applying high stress levels to the lens material when the two signals overlap, and yet leaving a pause in between for the occlusion to reestablish itself and vacuum build-up, thus improving efficiency of the following pulse application.

Still another alternative is to apply a continuous longitudinal signal with a pulsed torsional signal, or vice versa, a continuous torsional signal with a pulsed longitudinal signal. Continuous application of torsional ultrasound does not cause repulsion because tip 200 movement is oriented perpendicular to the direction of the engagement of tip 200 with the lens, and the pulsed applications of longitudinal ultrasound are short enough to prevent overheat or mechanical damage to the piezoelectric elements.

Finally, as discussed above, both the longitudinal and torsional drive signals can be applied continuously and simultaneously, with the amplitudes of the both signals being selected such that overheating and excessive mechanical stress on the system is reduced. If such a drive scheme is to be used, two sets of piezoelectric elements are preferred with the torsional signal being applied to one set, while longitudinal signal applied to the other set.

Although references have been made in the foregoing description to various embodiments, persons of ordinary skill in the art will recognize that insubstantial modifications, alterations, and substitutions can be made to the described embodiments without departing from the scope of embodiments. For example, persons of ordinary skill in the art will recognize that various capabilities and embodiments can be operated individually or in combination. For example, in an alternative embodiment, the embodiments directed to determining changes in aspiration vacuum and/or irrigation pressure can be combined with the "Thermal Watch" embodiments shown in FIGS. 7 and 8 and/or with the "Power On Demand" embodiments described and shown with reference to FIGS. 9-11. Similarly, the "Thermal Watch" embodiments described and shown with reference to FIGS. 7 and 8 can be combined with the Power On Demand embodiments described and shown with reference to FIGS. 9-11. Thus, embodiments can operate together or individually to provide the desired system functionality.

What is claimed:

1. A method of controlling a surgical system, the surgical system having an ultrasound handpiece, the ultrasound handpiece having a cutting tip for cutting tissue, the method comprising the steps of:
    establishing a threshold power level;
    monitoring a load on the cutting tip of the ultrasound handpiece by monitoring a voltage and a current drawn by the handpiece during a non-zero sense power interval, the sense power interval being between cutting power intervals;
    comparing the amount of power drawn by the handpiece and the threshold power level; and
    adjusting an amount of power delivered to the cutting tip of the ultrasound handpiece if the power drawn by the handpiece exceeds the threshold power level by enabling torsional vibration of the tip.

2. The method of claim 1, the threshold power level being based on the cutting tip being operated in saline or reference environment.

3. The method of claim 1, monitoring the amount of power drawn by the handpiece being determined by a linear calculation of multiplying the current and the voltage drawn by the ultrasound handpiece.

4. The method of claim 1, wherein the duty cycle of the output of the ultrasound handpiece remains constant or being controlled by a surgeon.

5. The method of claim 1, wherein adjusting the amount of power delivered to the cutting tip of the ultrasound handpiece comprises adjusting an amount of power up to a maximum amount of power requested by a user.

6. The method of claim 1, wherein the step of adjusting the amount of power comprises adjusting a stroke of the cutting pulse or interval following the non-zero sense interval.

7. The method of claim 1, further comprising the step of adjusting an amount of power to be delivered to the cuffing tip with a sensitivity coefficient.

8. The method of claim 1, wherein the step of monitoring the load comprises monitoring the load on the cutting tip of the ultrasound handpiece by monitoring a voltage and a current drawn by the handpiece during the non-zero sense power interval, the sense power interval having about the same duration as the cuffing power interval.

9. The method of claim 1, wherein the step of monitoring the load comprises monitoring the load on the cutting tip of the ultrasound handpiece by monitoring a voltage and a current drawn by the handpiece during the non-zero sense power interval, the sense power intervals being longer or shorter than the cutting power interval.

10. The method of claim 1, wherein the step of monitoring the load comprises monitoring the load on the cutting tip of the ultrasound handpiece by monitoring a voltage and a current drawn by the handpiece during non-zero sense power intervals having a fixed duration.

11. The method of claim 1, wherein the step of monitoring the load comprises monitoring the load on the cuffing tip of the ultrasound handpiece by monitoring a voltage and a current drawn by the handpiece during non-zero sense power intervals having a variable duration.

12. The method of claim 1, wherein the step of monitoring the load comprises monitoring the load on the cutting tip of the ultrasound handpiece by monitoring a voltage and a current drawn by the handpiece during a plurality of non-zero sense power intervals that are separate pulses between a plurality cutting pulses.

13. The method of claim 1, wherein the step of monitoring the load comprises monitoring the load on the cutting tip of the ultrasound handpiece by monitoring a voltage and a current drawn by the handpiece during the non-zero sense power interval immediately prior to the cutting interval.

14. The method of claim 1, wherein the step of monitoring the load comprises monitoring the load on the cutting tip of the ultrasound handpiece by monitoring a voltage and a current drawn by the handpiece during the non-zero sense power interval immediately following the cutting interval.

15. The method of claim 1, wherein the step of monitoring the load comprises monitoring the load on the cutting tip of the ultrasound handpiece by monitoring a voltage and a current drawn by the handpiece during a decay of the non-zero sense power interval.

16. The method of claim 15, further comprising the step of correlating a rate of decay of the non-zero sense power interval to the load drawn by the handpiece.

17. The method of claim 1, further comprising cutting tissue during the step of monitoring the load.

\* \* \* \* \*